(12) United States Patent  (10) Patent No.: US 8,734,324 B2
Muller  (45) Date of Patent: May 27, 2014

(54) APPARATUS FOR APPLYING TRACTION TO A PENIS

(75) Inventor: Jes Bech Muller, Klampenborg (DK)

(73) Assignee: JBM Holding, Klampenborg (DK)

( * ) Notice: Subject to any disclaimer, the term of this patent is extended or adjusted under 35 U.S.C. 154(b) by 702 days.

(21) Appl. No.: 13/002,478

(22) PCT Filed: Jul. 3, 2009

(86) PCT No.: PCT/EP2009/058432
§ 371 (c)(1),
(2), (4) Date: Mar. 8, 2011

(87) PCT Pub. No.: WO2010/000845
PCT Pub. Date: Jan. 7, 2010

(65) Prior Publication Data
US 2011/0172489 A1  Jul. 14, 2011

(30) Foreign Application Priority Data

Jul. 3, 2008 (EP) .................................. 08159669
Oct. 17, 2008 (DK) ................................ 2008 01450

(51) Int. Cl.
A61F 5/00 (2006.01)
(52) U.S. Cl.
USPC ....................................................... 600/39
(58) Field of Classification Search
USPC ............... 600/38–41; 128/898; 601/107, 108, 601/110, 111, 115, 116, 86, 90, 98, 66
See application file for complete search history.

(56) References Cited

U.S. PATENT DOCUMENTS

| 3,274,998 | A | 9/1966 | Grier, Jr. | |
| 3,730,198 | A * | 5/1973 | Johnston et al. | 135/69 |
| 4,449,521 | A * | 5/1984 | Panzer | 600/39 |
| 6,416,460 | B1 | 7/2002 | Jochum | |
| 7,276,040 | B2 | 10/2007 | Gomez-de-Diego | |
| 2010/0108850 | A1 * | 5/2010 | Holzapfel | 248/523 |

FOREIGN PATENT DOCUMENTS

| CN | 1284517 C | 11/2004 |
| CN | 2749344 Y | 1/2006 |
| DE | 689 07 862 | 4/1994 |
| DE | 196 20 719 | 12/1996 |
| DE | 196 18 352 | 11/1997 |
| DE | 295 21 655 | 6/1998 |
| EP | 1473000 A1 | 11/2004 |
| GB | 2133289 A | 7/1984 |
| NL | 1029901 | 3/2007 |
| WO | WO 95/05134 | 2/1995 |
| WO | WO 96/26691 | 9/1996 |
| WO | WO 01/90587 A1 | 11/2001 |
| WO | WO 03/073967 | 9/2003 |

* cited by examiner

Primary Examiner — Samuel Gilbert
(74) Attorney, Agent, or Firm — Muncy, Geissler, Olds & Lowe, P.C.

(57) ABSTRACT

An apparatus (1) for applying traction to a penis, comprising a base member (10), a glans' retaining member (20) and a telescoping connection member (30 is disclosed.

13 Claims, 21 Drawing Sheets

APPARATUS FOR APPLYING TRACTION TO A PENIS

FIELD OF THE INVENTION

The present invention relates to an apparatus for applying traction to a penis, comprising a base member, a glans retaining member and a telescoping connection member. Moreover, the present invention relates to a telescoping connection member an apparatus for applying traction to a penis. Furthermore, the present invention relates to a retaining member for an apparatus for applying traction to a penis.

BACKGROUND OF THE INVENTION

A number of devices are known in the field of apparatuses for penile elongation. Examples of such apparatuses are disclosed in U.S. Pat. No. 4,449,521 A and U.S. Pat. No. 7,276,040 B2. A common problem of these devices is that they are difficult and/or cumbersome to mount on the penis and adjust with respect to the distance between a base part supporting against the base of the penis and a part that fixates or supports the glans of the penis.

U.S. Pat. No. 7,276,040 B2 discloses an apparatus for applying traction to a penis where a number of separate pieces, of variable length that are screwed together to adjust the distance between a base and a glans fixating part. This is cumbersome, and fine adjustment of the system is difficult. Many attempts, using the various pieces, must be made in order to make a fine adjustment. It goes without saying that if the adjustment is not very exact, the use will either be very painful to the user or there will be no effect of the use. In order to obtain a precise, useful adjustment a large number of pieces must be available. Such extension pieces may further easily be lost.

U.S. Pat. No. 4,449,521 discloses an apparatus for applying traction to a penis (not in order to provide a permanent elongation, but for supporting the penis during intercourse) wherein two telescoping rods or tubes are used to adjust the distance between a base and a glans fixating part. The two rods/tubes are fixed at a desired distance from each other by a fixation screw. This device may provide a fine adjustment. However, it is highly disadvantageous that a user needs to utilise addition tools to adjust the apparatus. Further, there is a risk that the set screw which projects sideways from the rods/tubes may scratch or otherwise provide discomfort for the user, or stick to e.g. clothing. The U.S. Pat. No. 4,449,521 apparatus is covered by a pliable material to prevent damage to body tissues. Thus operation of the set screw is impeded, since the screw must be operated through the pliable material, or the material must be breeched providing scratching edges etc. Hence an improved apparatus for applying traction to a penis would be advantageous, and in particular a more efficient and or reliable adjustment of the distance between the base and the fixation means would be advantageous.

OBJECT OF THE INVENTION

It is an object of one or more embodiments of the present invention to overcome the above described disadvantages of the prior art apparatuses.

Moreover, it is an object of one or more embodiments of the present invention to provide a retaining member for an apparatus for applying traction to a penis that is easily adjustable, without loose parts.

Furthermore, it is an object of one or more embodiments of the present invention to provide a retaining member apparatus for applying traction to a penis that is adjustable without the use of separate tools.

Additionally, it is an object of one or more embodiments of the present invention to provide an alternative to the prior art

SUMMARY OF THE INVENTION

In a FIRST aspect the present invention relates to a telescoping connection member for an apparatus for applying traction to a penis with a base and a glans, the apparatus comprising:
a base member adapted to be arranged around the base of the penis;
a retaining member for fixation and support of the glans of the penis; and
at least one telescoping connection member arranged between the base member and the retaining member, each the telescoping connection member having a longitudinal axis (A);
the telescoping connection member comprising:
a first tube part and a second tube part, the first tube part being slidably arranged in the second tube part;
a first spring connected to the first tube part, the first spring being compressible in a direction transverse to the longitudinal axis (A) of the telescoping connection member; and
at least one first engagement means arranged on the spring, and a plurality of second engagement means arranged in the second tube part,
wherein each first engagement means is adapted to engage any of the second engagement members so as to releasably lock the first tube part against longitudinal movement relative to the second tube part.

In one embodiment, first engagement means defines a knob, and the second engagement means defines apertures formed in the inner wall of the second tube part.

In a further embodiment, the knob has a rounded or inclined surface, which facilitates travel of the knob in a direction transverse to the longitudinal axis A of the telescoping connection member against compression of the spring when moving said first tube part in relation to said second tube part.

In a further embodiment, the first tube part is rotatable in relation to the second tube part, and wherein the inclined surface extends parallel to longitudinal axis A of the telescoping connection member, so that rotation of the first and second tube parts with respect to each other facilitates radial travel of the knob in a direction transverse to the longitudinal axis of the telescoping connection member.

In a further embodiment, the spring is U-shaped, having a set of resilient arms with first engagement means arranged on each arm, and where a first and second plurality of second engagement means are arranged oppositely in the second tube part.

In a further embodiment, the retaining member comprises third engagement means adapted to cooperate with either of a plurality of fourth engagement means on the second tube part and/or on the first tube part to prevent rotation of the first tube part with respect to the second tube part.

In a further embodiment, having two telescoping connecting members connectable to said retaining member, wherein a plurality of fourth engagement means are formed on each of the second tube parts, and where each of the retaining members comprises third engagement means each adapted to cooperate with either of the plurality of fourth engagement means on the second tube parts, such that the second tube parts are prevented from rotation with respect to the first tube parts.

In a further embodiment, the third engagement means are knobs, and the fourth third engagement means are apertures formed in the outer surface of the second tube part.

In a further embodiment, the fourth engagement means are apertures formed through the second tube part.

In a further embodiment, the fourth engagement means also serve as the second engagement means.

In a further embodiment, the retaining member comprises at least one sliced tube part adapted to click-on at a second tube part of a telescoping connecter member to prevent rotation of the first tube part with respect to the second tube part.

In a further embodiment, the third engagement means is a knob formed on the inside of the sliced tube part, adapted for engaging at least either of a plurality of fourth engagement members in the form of apertures on the second tube part in order to prevent rotation of the second tube part with respect to the first tube part, and wherein the sliced tube part has a first and a second end, and where the third engagement means is formed in the proximity of either the first or the second end.

In a further embodiment, one telescoping connecting member, is provided with a first and second tube connected rotatably with respect to each other, wherein the fourth engagement means comprises:
  a plurality of apertures formed through the second tube part, and
  a plurality of apertures or an elongate groove formed in the outer surface of the first tube part,
and where the third engaging means is a knob adapted to extend though either of the apertures in the second tube part and engage with the groove or either of the plurality of apertures formed in the outer surface of the first tube part.

In a SECOND aspect the present invention relates to a retaining member for an apparatus for applying traction to a penis with a base and a glans, the apparatus comprising:
  a base member adapted to be arranged around the base of the penis,
  a retaining member for fixation and support of the glans of the penis, and
  at least one elongate connection member arranged between the base member and the retaining member, the connection member having a longitudinal axis (A) and a proximal end near the base member and an opposite distal end;
wherein said retaining member comprises:
  a first end and a second end opposite said first end;
  connecting means for releasably connecting said retaining member to the distal end of said connection member, the connecting means being arranged at the first end of said retaining member, and comprising locking means for locking the retaining member against movement relative to the connecting member along the longitudinal axis in at least one direction; and
  glans fastening means which is arranged at the second end of said retaining member.

In one embodiment, the locking means defines a knob or an aperture cooperating with a corresponding aperture or knob, respectively, on the connection member so as to lock the retaining member relative to the connecting member.

In another embodiment, the retaining member is adapted to allow a user to fasten the connection member in either of:
  a first position in which the first end is positioned closer to the base member than the second end, or
  a second position in which the second end is positioned closer to the base member than the first end.

The invention according to the second aspect may comprise the following embodiments.

Embodiment 1

A retaining member for an apparatus for applying traction to a penis, comprising
  a base member adapted to be arranged around the base of the penis;
  at least one elongate connection member arranged between the base member and the retaining member, the connection member having a longitudinal axis (A) and a proximal end near the base member and an opposite distal end; and
  a retaining member for fixation and support of the glans of the penis,
wherein said retaining member comprises
  a first end and a second end opposite said first end, and
  means for releasably connecting said retaining member to the distal end of said connection member,
wherein said glans fastening means are arranged at said second end of said retaining member and in that said means for releasably connecting said retaining member to the distal end of said connection member are arranged at the first end of said retaining member.

Embodiment 2

A retaining member according to embodiment 1, wherein said means for releasably connecting said retaining member to the distal end of said connection member comprises means for locking said retaining member against movement relative to said connection member along longitudinal axis (A).

Embodiment 3

A retaining member according to embodiment 2, wherein said means for locking said retaining member against movement relative to said connection member cooperates with means on the connection member.

Embodiment 4

A retaining member according to anyone of embodiments 1-3, wherein said means for releasably connecting said retaining member to the distal end of said connection member is adapted for snapping on to said connection member.

EMBODIMENT 5

A retaining member according to any of embodiments 1-4, wherein said means for releasably connecting said retaining member to the distal end of said connection member is a sliced tube part.

Embodiment 6

A retaining member according to embodiment 5, wherein said sliced tube part projects from said glans fastening means.

Embodiment 7

A retaining member according to anyone of embodiments 1-4, wherein said means for releasably connecting said retaining member to the distal end of said connection member is a clip.

Embodiment 8

A retaining member according to embodiment 7, further comprising a second clip arranged at said second end of said retaining member.

EmbodimenT 9

A retaining member according to any of embodiments 1-8, wherein there are two connection members and two means for releasably connecting said retaining member to the distal ends of said connection members.

In a THIRD aspect, the present invention relates to an apparatus for applying traction to a penis with a base and a glans, the apparatus comprising:
- a base member adapted to be arranged around the base of the penis;
- a retaining member for fixation and support of the glans of the penis, the retaining member being according to second aspect of the invention; and at least one telescoping connection member arranged between the base member and the retaining member, each retaining member being according to the first aspect of the invention.

In a FOURTH aspect, the present invention relates to a kit comprising:
- a base member adapted to be arranged around the base of the penis;
- a retaining member for fixation and support of the glans of the penis, the retaining member being according to second aspect of the invention; and
- at least one telescoping connection member arranged between the base member and the retaining member, each retaining member being according to the first aspect of the invention.

Throughout this document the terms "comprising" or "comprises" do not exclude other possible elements or steps. Also, the mentioning of references such as "a" or "an" etc. should not be construed as excluding a plurality.

In the context of this text, the term aperture should be understood as an opening or hole, that mayor may not extend through a material in which is formed. Thus, 'aperture' may cover an indentation, i.e. blind hole, or a through going hole. Where, in this text the term should be understood as a through going hole this is specified.

BRIEF DESCRIPTION OF THE FIGURE

The invention will now be described in further detail with reference to the figures in which.

The figures show one way of implementing the present invention and is not to be construed as being limiting to other possible embodiments falling within the scope of the attached claim set.

DETAILED DISCLOSURE OF THE INVENTION

Figure 1:
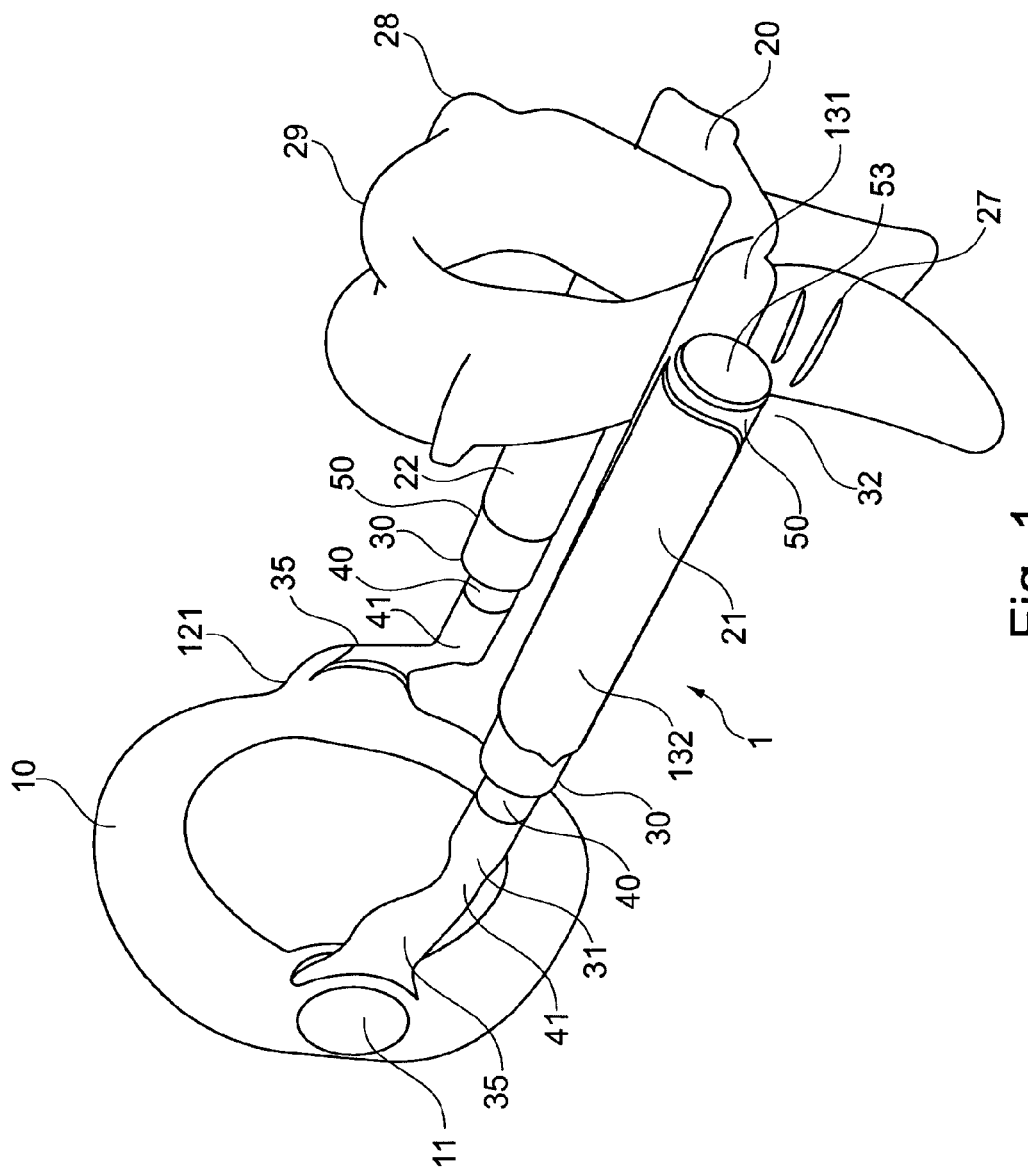
FIG. 1, in a perspective view, shows an assembled apparatus for applying traction to a penis, with a retaining member according to an embodiment of the invention.
Figure 2:
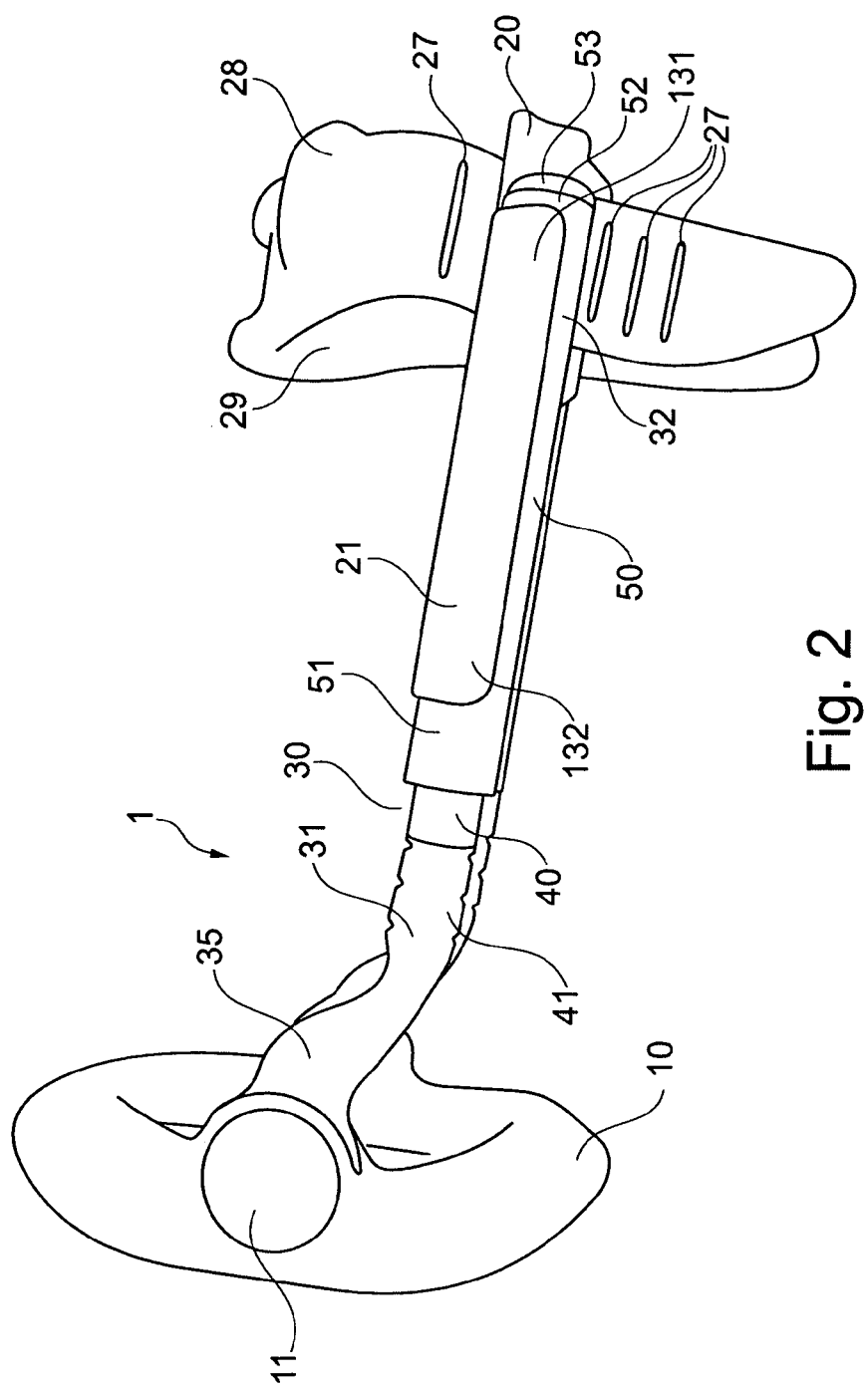
FIG. 2 shows the apparatus of FIG. 1 seen from the side.
Figure 3:
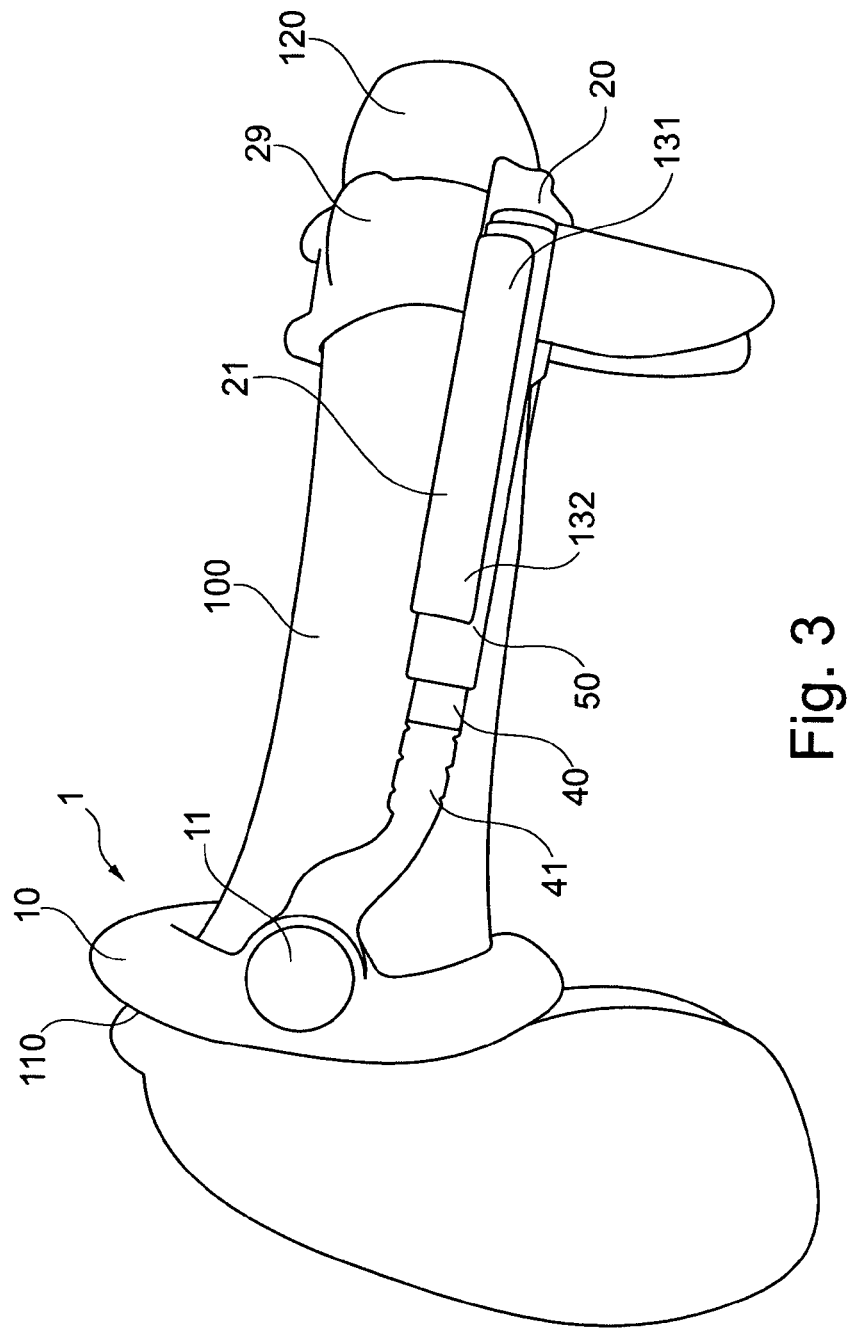
FIG. 3 shows the apparatus of FIGS. 1 and 2 mounted and in use, as seen from the side.
Figure 4:
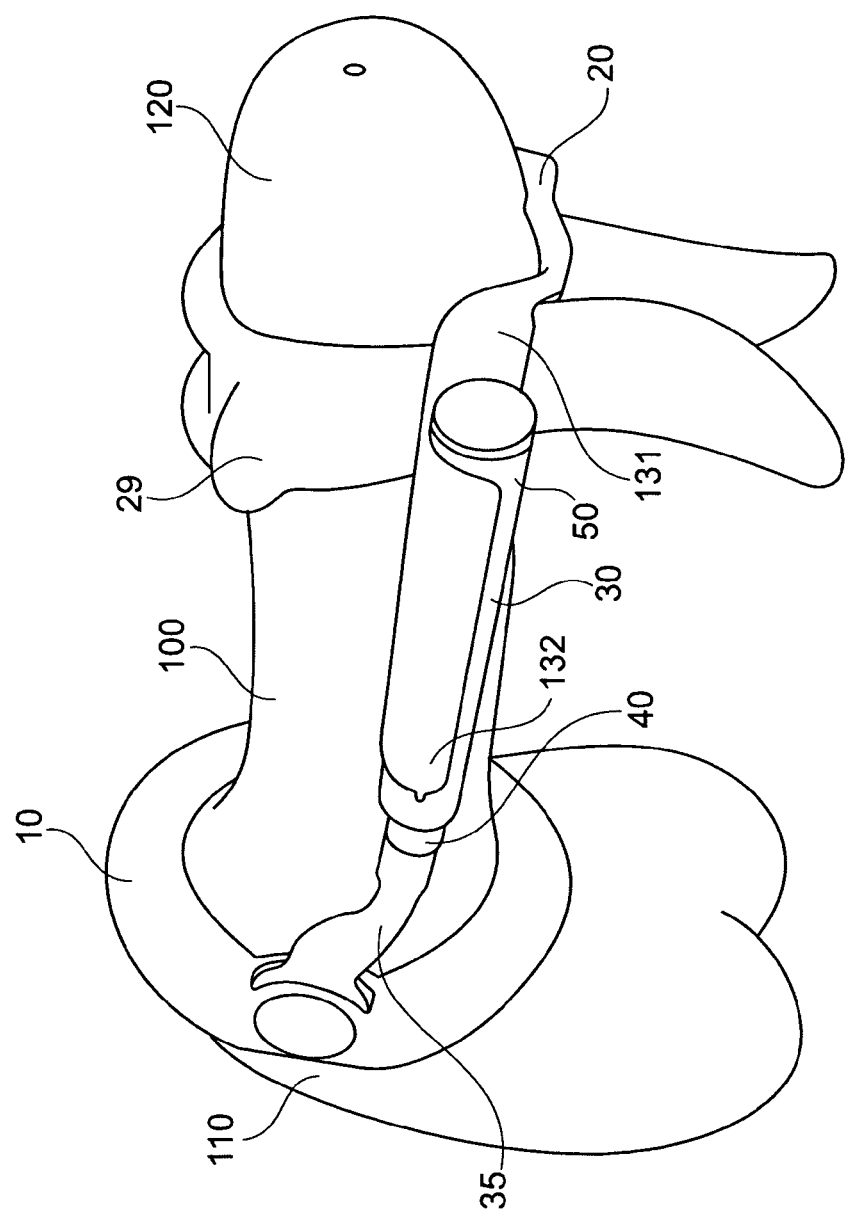
FIG. 4 shows the apparatus of FIGS. 1 and 2 mounted and in use, and as seen from a side-front view.
Figure 5:
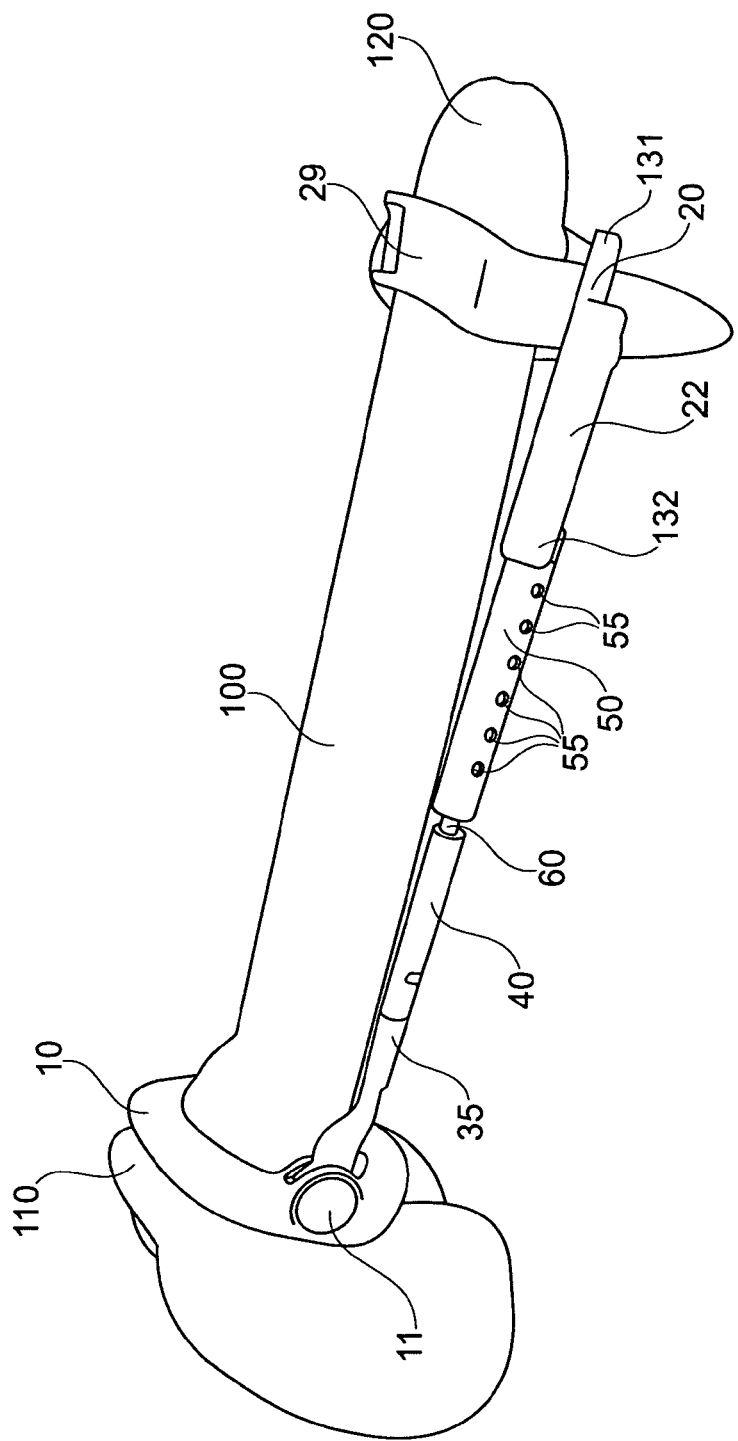
FIG. 5 shows the apparatus of FIGS. 1 and 2 mounted and in use in a most extended position.

In FIG. 1, an apparatus 1 for applying traction to an elongate body member, such as a penis, according to an embodiment of the invention is shown. The apparatus 1 comprises a base member 10 adapted to be arranged around the base 110 of a penis 100. The base member 10 may preferably, and as shown be a substantially ring shaped member, but may also be formed using other suitable shapes, e.g. an open ring structure or discrete pads or the like. The main issue is that the base member should form a comfortable base against the base of a penis in order to avoid discomfort for a user of the apparatus 1.

The apparatus 1 further comprises a retaining member 20 which is adapted for fixation and support of a glans 120 of a penis 100. The retaining member 20 comprises means 29 for fastening or retaining the glans of a penis 100, by fastening around the shaft of the penis immediately behind or proximal to the glans 120, to the retaining member 20, and means for connection to the base member, via connection members 30, to be described below. The glans fastening means 29 may, as shown in the accompanying figures, be a resilient band, releasably secured to the body part 23 of the retaining member 20 via openings 26, in the body part 23, and protrusions 27, cooperating with said openings 26, preferably in the form of transversely oriented protrusions 27 on the resilient band constituting the glans fastening means 29. The glans fastening means may further be provided with handles 28, to ease adjustment of the glans fastening means 29 immediately behind the glans 120 of a user's penis.

The apparatus 1 further comprises at least one, and in the embodiment shown in the FIGS. 1-10, two telescoping connection members 30 arranged between the base member 10 and the retaining member 20, in order to provide a separation of the base member 10 and the retaining member 20 during use and to provide traction to a penis 100. The telescoping connection members 30 have first, proximal ends 31 and second, distal ends 32, and a longitudinal axis A, which during use is intended to be substantially parallel to an elongate axis of the extended penis 100 of a user. The connection members 30 are connected to the base member 10 via an articulated joint 11, 12 formed on the base, and an arm 35 at the proximal end 31 of the connection member 30.

The connection member 30 comprises a first tube part 40 and a second tube part 50. The first tube part 40 has a proximal end 41 and a distal end 42. Likewise, second tube part 50 has a proximal end 51 and a distal end 52. The second tube part is hollow and has an inner sidewall 54 and an outer sidewall 56.

In the embodiment shown in FIGS. 1-10, the proximal end of the first tube part 40 is connected via arm 35 to the base member 10 via the articulated joint 11, 12. The distal end 41 of the first tube part is connected to the proximal end 51 of the second tube part 50, such that the first 40 and second 50 tube parts are slideably engaging each other, in a telescoping manner. In the shown embodiment, the first tube part 40 is slidably arranged in said second tube part 50. Further, in the shown in shown embodiment, the first 40 and second 50 tube parts are also rotatably engaging each other. Thus, adjustment of the length of the connection member is allowed. Below it will be described how the first 40 and second 50 tube parts are locked in a desired position.

The distal end 52 of the second tube part 50 is connectable to the retaining member 20. In the shown embodiment distal end 52 of the second tube part 50 is closed with a plug 53. This however, is optional. In other embodiments the distal end may be open or it may be formed as a closed end (not shown).

A first spring 60 is connected to, and extended from, the distal end 42 of the first tube part 40. The first spring 60 is radially compressible, that is compressible in a direction transverse to the longitudinal axis A of the telescoping connection member 30. The first spring 60 extends distally from the first tube part 40, and into the second tube part 50, and is adapted to be slideably and rotationally arranged inside the second tube part in a manner described in further detail below. The first spring 60 is fixed against rotation with respect to the first tube part 40. However, the first spring 40 may be slideably connected to the first tube part 40 via a second spring 70, preferably providing a biasing in the distal direction along the longitudinal axis A. This is the case in the embodiment shown in the FIGS. 1-10; however, this may be an optional feature in other embodiments.

In the shown embodiment, the first spring 60 has a body part 61, and a U-shaped part, having a set of resilient arms 63, 64. The body part forms a connection to the first tube part 40. A set of first engagement means 65, 65' preferably in the form of a knob or protrusion is formed at the end of arms 63, 64, and extending in a direction transverse to the longitudinal direction A of the connection arms 30. A first plurality of second engagement means 55 in the form of apertures are formed in line on one side of the inner sidewall 54 of the second tubular part 50, the apertures being adapted to cooperate with the knob, forming the first engagement means 65 on the arm 63. A second plurality of apertures 55' are formed in line on the other side of the inner sidewall 54 of the second tubular part 50, diametrically across from (oppositely) the first plurality of apertures 55, the apertures being adapted to cooperate with the knob, forming the first engagement means 65' on the arm 64.

In the embodiment shown, the second engagement means 55, 55' are seven pairs of apertures formed oppositely on each second tube member 50. In other embodiments there may be more or less apertures, depending on the length of the second tube part 50 and the desired accuracy of adjustment. Also, the apparatus may be delivered with different sets of second tubes 50, of different lengths.

The U-shaped part of the first spring 60 provides a biasing of a the resilient arms 63, 64, and thereby the set of first engagement means 65, 65' in a direction transverse to the longitudinal axis A and towards the inner sidewall 54 of the second tubing 50 and the second engagement means 55, 55' formed in the inner sidewall 54 of the second tube part 50.

The apertures forming the second engagement means 55, 55' may in a preferred embodiment, and as shown in FIGS. 1-10, be formed as through going holes from the inner sidewall 54 to and through the outer sidewall 56 of the second tube 50. In other embodiments (not shown) they may be formed as indentations in the inner sidewall 54 of the second tube part 50. In yet other embodiments (not shown) the second engagement means 55, 55' may be formed as knobs or protrusions formed on the inner sidewall 54 of the second tube part 50, in which case the first engagement means 65, 65' may be formed as apertures on the first spring 60.

Thus, the length of a connection member 30 may be adjusted by sliding the first tube part 40 in relation to the second tube part 50. The resiliency of the first spring 60, i.e. the arms 63, 64 will force the first engagement means 65, 65' into engagement with a set of the second engagement means 55, 55', when the first and second engagement means 65, 65'; 55, 55' are aligned, to releasably lock the first tube part 40 and the second tube part 50 against sliding with respect to each other. This locking relation may be released by a pull, push or a twist (rotation) of the first part 40 with respect to the second tube part 50, of sufficient force to overcome the force provided by the resiliency of the arms 63, 64 of the first spring 60 and the friction between the knobs and the apertures.

In embodiments where the second engagement means 55, 55' are through-going holes the locking relation may further be released by pushing the knobs out of engagement with the aperture, e.g. by using a pointed instrument that may extend through the hole/aperture forming the second engagement means 55, 55'.

Figure 10:
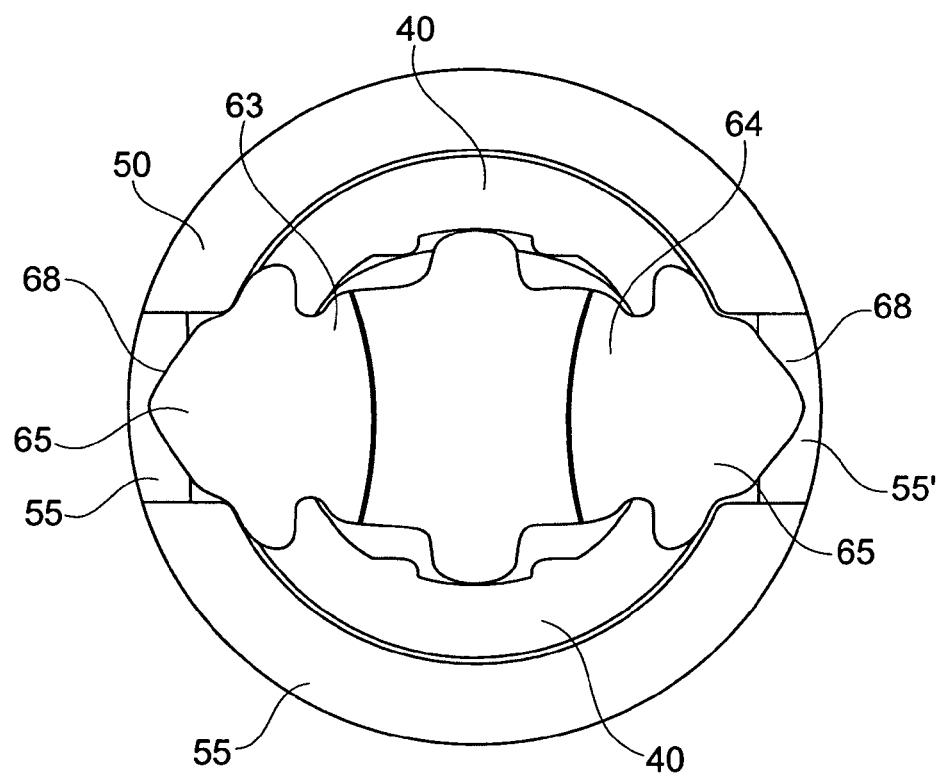
FIG. 10 is a section through a telescoping connecting member of the apparatus shown in FIGS. 1-9, showing details of engagement means.
Figure 11:
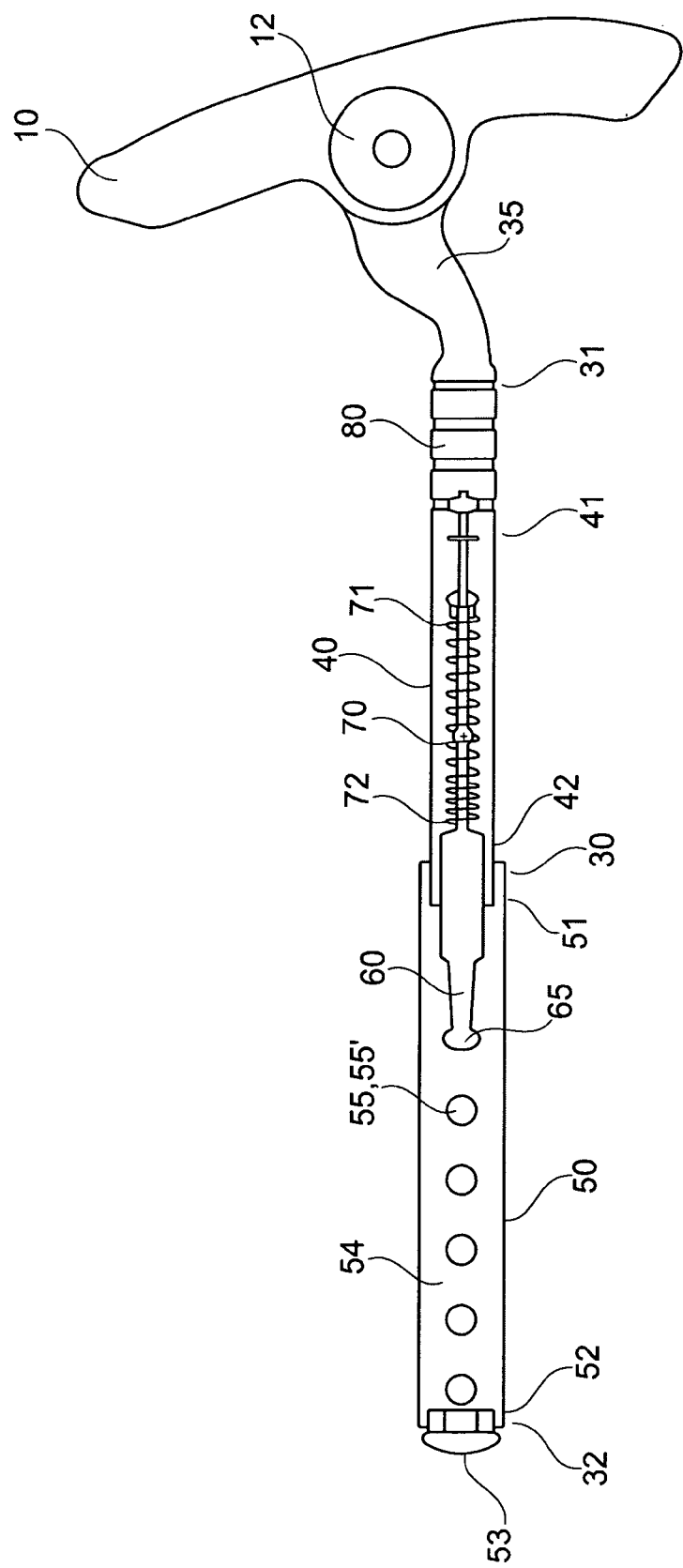
FIG. 11, in a sectional side view, shows details of a biasing mechanism of an apparatus for applying traction to a penis.

In a preferred embodiment, and as shown in FIG. 10, the knobs forming the first engagement means 65, 65' may be formed with a rounded surface or an inclined surface 68 at the outermost tip of the knob. Thereby the travel of the knob (first engagement means 65 is facilitated in a direction transverse to the longitudinal axis A of the connection member 30 against compression of the spring 60, i.e. in an inward direction, when moving said first tube part 40 in relation to said second tube part 50.

In alternative embodiment (not shown), and where knobs are arranged on the inside 54 of the second tube part 50 for cooperation with an aperture on the first spring 6, these knobs may be provided with inclined surfaces, and/or the apertures may be provided with a rounding or an inclined surface.

Figure 6:
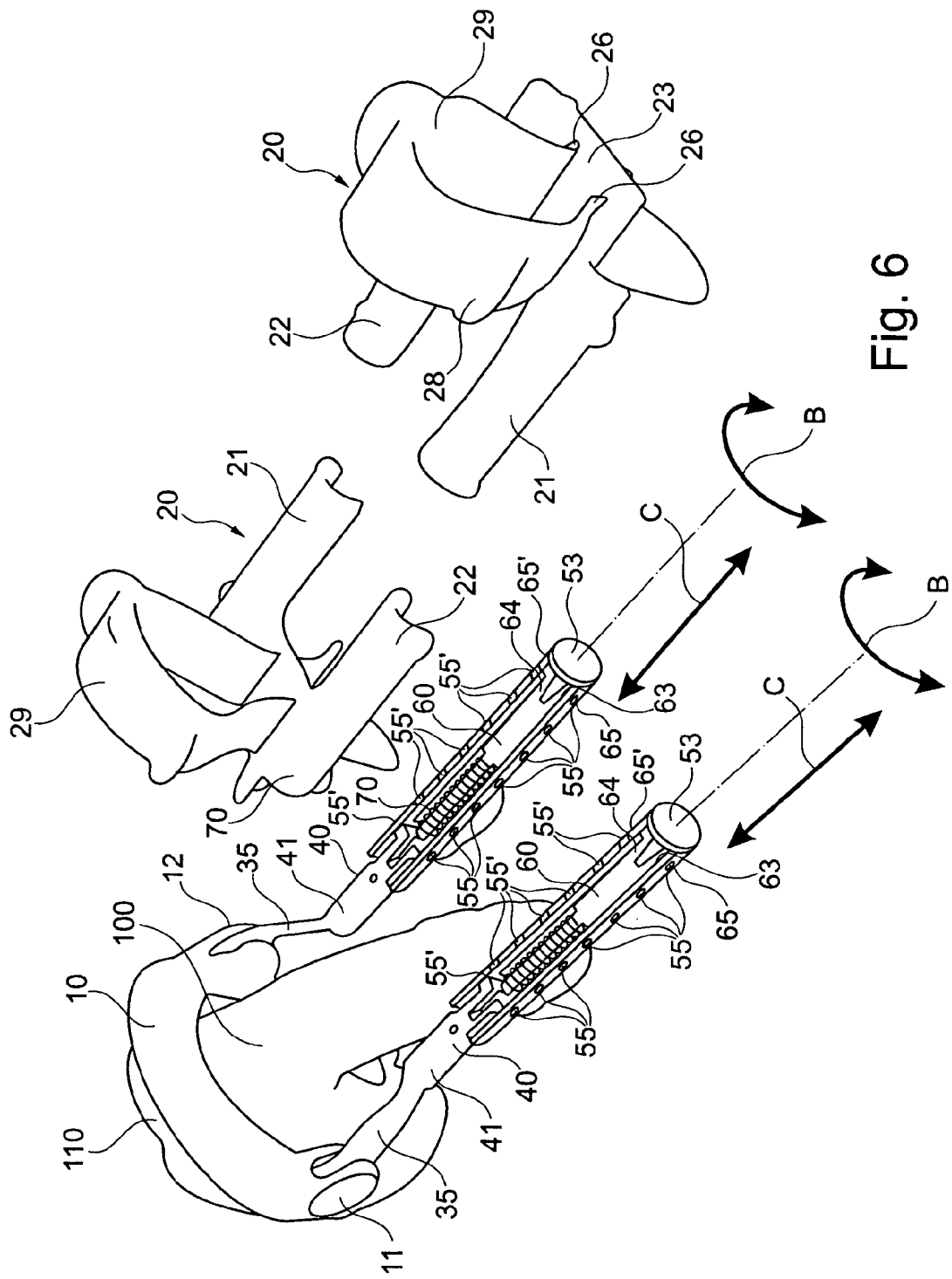
FIG. 6, in a perspective and partially sectioned view, shows details of the apparatus shown in FIGS. 1 and 2, with a glans retaining member being dismounted, and shown in two different optional orientations, a connecting arm being in its most retracted state.
Figure 7:
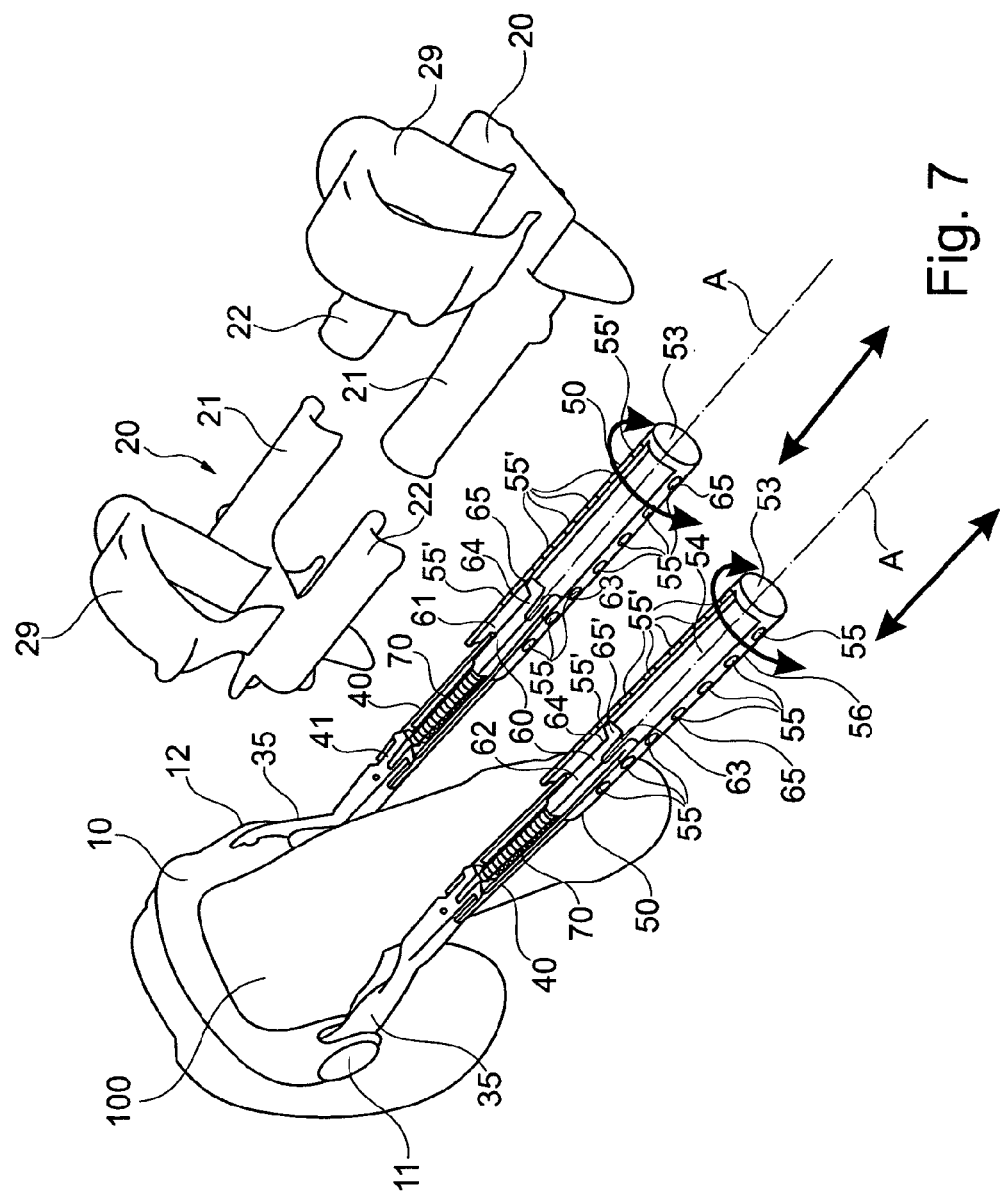
FIG. 7, in a perspective and partially sectioned view, shows details of the apparatus shown in FIGS. 1 and 2, with a glans retaining member being dismounted, and shown in two different optional orientations, a connecting arm being in a distended state.

In yet an embodiment the inclined surface 68 extends parallel to longitudinal axis A of the connection member 30, so that rotation of the first and second tube parts 40, 50 with respect to each other facilitates radial travel of the knob 65, i.e. travel in a direction transverse to the longitudinal axis A of the connection member 30, and inward. Thereby adjustment of the length of the connection members 30 may be provided as indicated by the arrows B, C in FIGS. 6 and 7. In FIG. 6 the first and second tube parts 40, 50 are in a position where the second tube parts 50 cover the first tube parts 40, such that the connection member 30 is in it shortest possible configuration. The knobs forming the first engagement members 65, 65' are engaging the distal-most apertures forming the second engagement means 55, 55', whereby the first and second tube parts are releasably locked against sliding with respect to each other. By rotating the second tube member 50 with respect to the first tube member 40 as indicated by arrows B, the knobs on the first spring 60 are brought out of engagement with apertures in the second tube part 50. This is facilitated by the inclined surfaces parallel with the elongate axis A on the knobs. Thereby, the first and second tube parts 40, 50 may be slid along elongate axis A, with respect to each other to adjust the length of the connection member 30, as indicated by arrows, C. In FIG. 7, the second tube part 50 has been slid relative to the first tube part 40 with respect to the configuration shown in FIG. 6. In FIG. 7 the knobs of spring 60 engages a second set of apertures 55,55', seen from the proximal end 51 of the second tube part 50. Thereby the connection members 30 have been extended in length.

The retaining member 20 comprises means for connection to the second tube parts 50 of the connection members 30, preferably, and as shown in FIGS. 1-9 in the form of sliced tube part 21, 22 adapted to click-on at the second tube parts 50. Thus, when the connection members 30 has been adjusted the length or distance between the base member 10 and the retaining member 20, and thereby the distance between the base 110 of the penis 100 and the glans may be kept constant and under strain in order to provide an elongation of the penis, at least over time. By the click-on function of the sliced tubes 21, 22 a very easy mounting of the retaining member 20 to the connecting members 30 is obtained. Other forms of connection means for connecting the connecting member 30 and the retaining member 20 may be provided e.g. by a tube, such as a tube providing a blind hole, that may be slid over the distal end of the second tube part 50 in alternative embodiments (not shown).

In an embodiment third engagement means 25 are formed on the retaining means 20 on the connecting mean for connecting the retaining means 20 to the connecting members 30, the third engagement means 25 being adapted to cooperate with either of a plurality of fourth engagement means on the outer surface 56 of the second tube part 50. Thereby, the first tube part 40 may be prevented from rotation with respect to the second tube part 50, which will then prevent the disengagement of the first engagement means 65, 65' from the second engagement means 55, 55', and thereby prevent that the first tube part 40 is slidable relative to the second tube part. Thus the lengths of the connection members 30 may be locked, when the retaining means 20 are mounted to the connection members 30 with the third engagement means 25 engaging the fourth engagement means.

The third engagement means 25 are preferably inwardly extending knobs on the connecting means, connecting the retaining member 20 to the connection members 30, and the fourth engagement means are preferably apertures formed in line in the outer surface 56 of the second tube, and adapted for cooperation with the knobs forming the third engagement means.

In an alternative embodiment (not shown), the third engagement means 25 may be apertures formed in an inner surface of the connecting means, connecting the retaining member 20 to the connection members 30, which apertures may be adapted for cooperation with knobs or protrusions formed in line on the outer surface of the second tube member 50

Preferably, and as shown in FIGS. 1-10, the fourth engagement means are apertures formed through the second tube part 50 from the outer sidewall 56 to and through the inner sidewall 54. Thereby the fourth engagement means also serve as the second engagement means 55.

Figure 20:
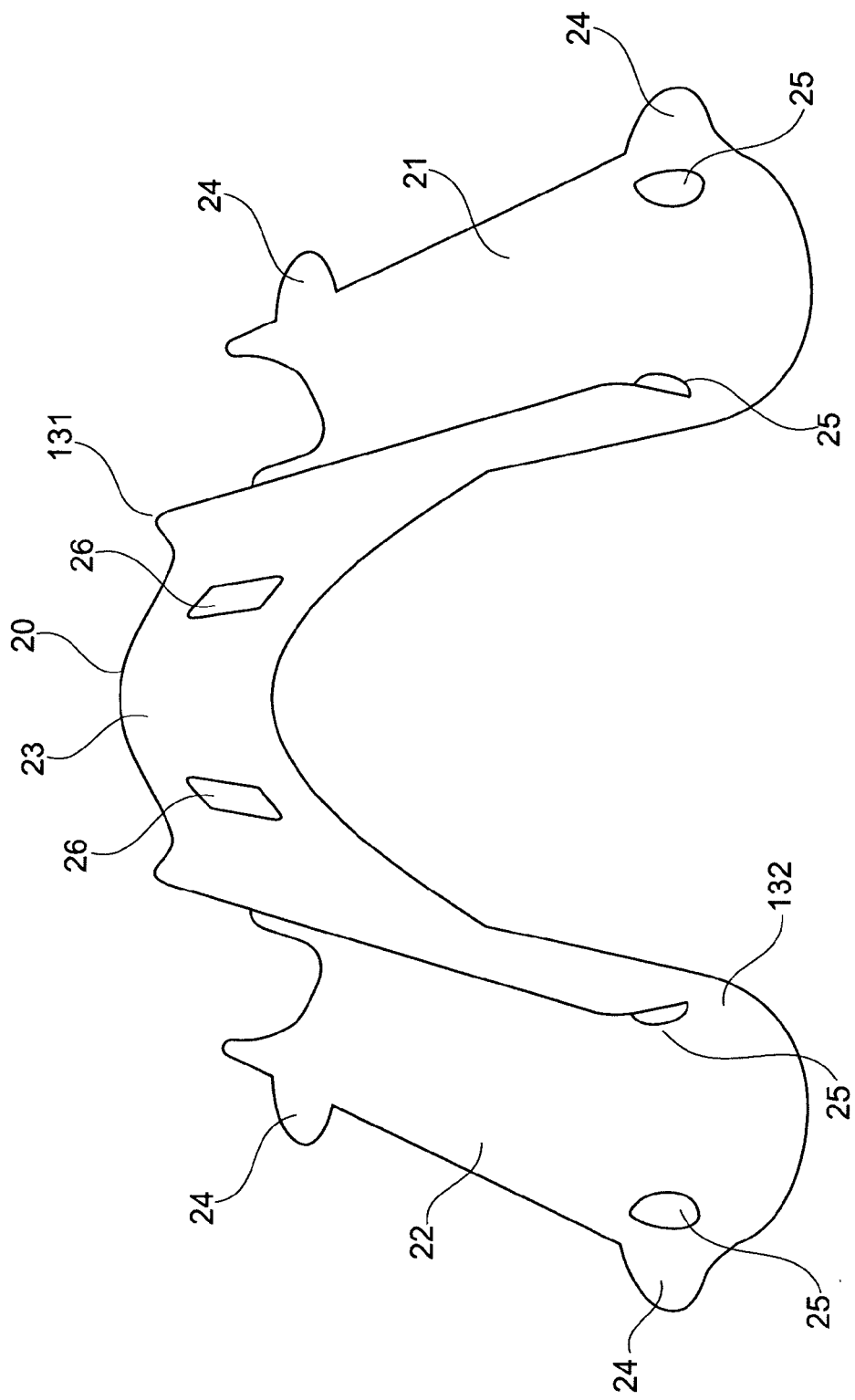
FIG. 20, in a perspective view, show a glans retaining member from below.
Figure 21:
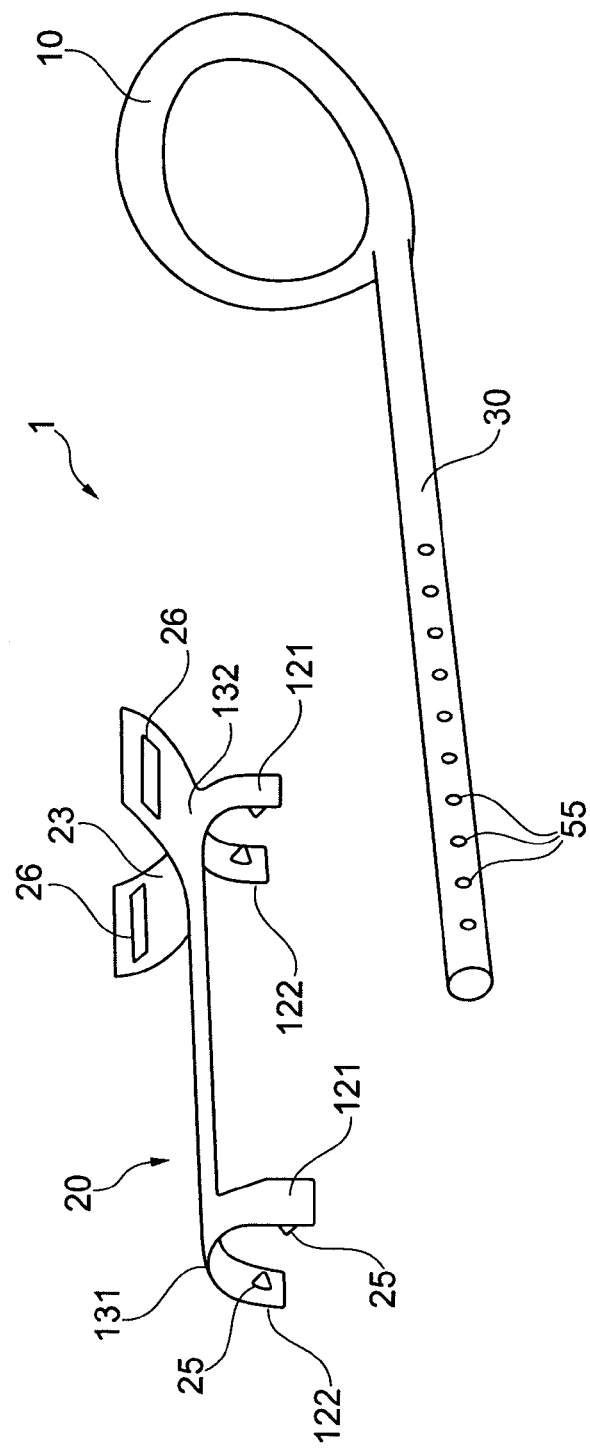
FIG. 21 shows a retaining member and other parts of an apparatus for applying traction to a penis according to another embodiment of the invention.

The third engagement means 25 are preferably formed on the inner surface of sliced tube parts 21, 22 of the retaining member 20. In an advantageous embodiment, and as shown in FIG. 20 the third engagement means 25 are knobs or protrusions formed on the inner surface of sliced tube parts 21, 22. As shown there may preferably be four third engagement means 25 protrusions, corresponding to the second/fourth engagement means 55 on the second tube part 50. The retaining member 20 preferably further is provided with handles 24 to facilitate a pull and/or push the retaining member 20 in a distal or a proximal direction for certain adjustment procedures, to be described below.

The sliced tube parts 21, 22 of the retaining member 20 each have first and a second ends. Preferably the third engagement means 25 are formed in the proximity of either the first or the second end. Thereby, by turning the retaining member 180°, different configurations, where the apparatus 1 has different lengths or distances between the base and the fastening means 29 of the retaining member 20, may be obtained. This can be illustrated by comparing FIGS. 1-4, where the retaining member has been mounted on the connecting members 30 to obtain one configuration, with FIG. 5 in which the retaining member has been turned 180° with respect to the configuration in FIGS. 1-4, thereby obtaining a maximum distance between the glans fastening means 29 on the retaining member 20 and the base member 10. This may also by illustrated by FIGS. 6 and 7 wherein two different orientations of the retaining member is shown. Thereby the overall flexibility of the adjustment of the apparatus has been considerably improved.

Figure 8:
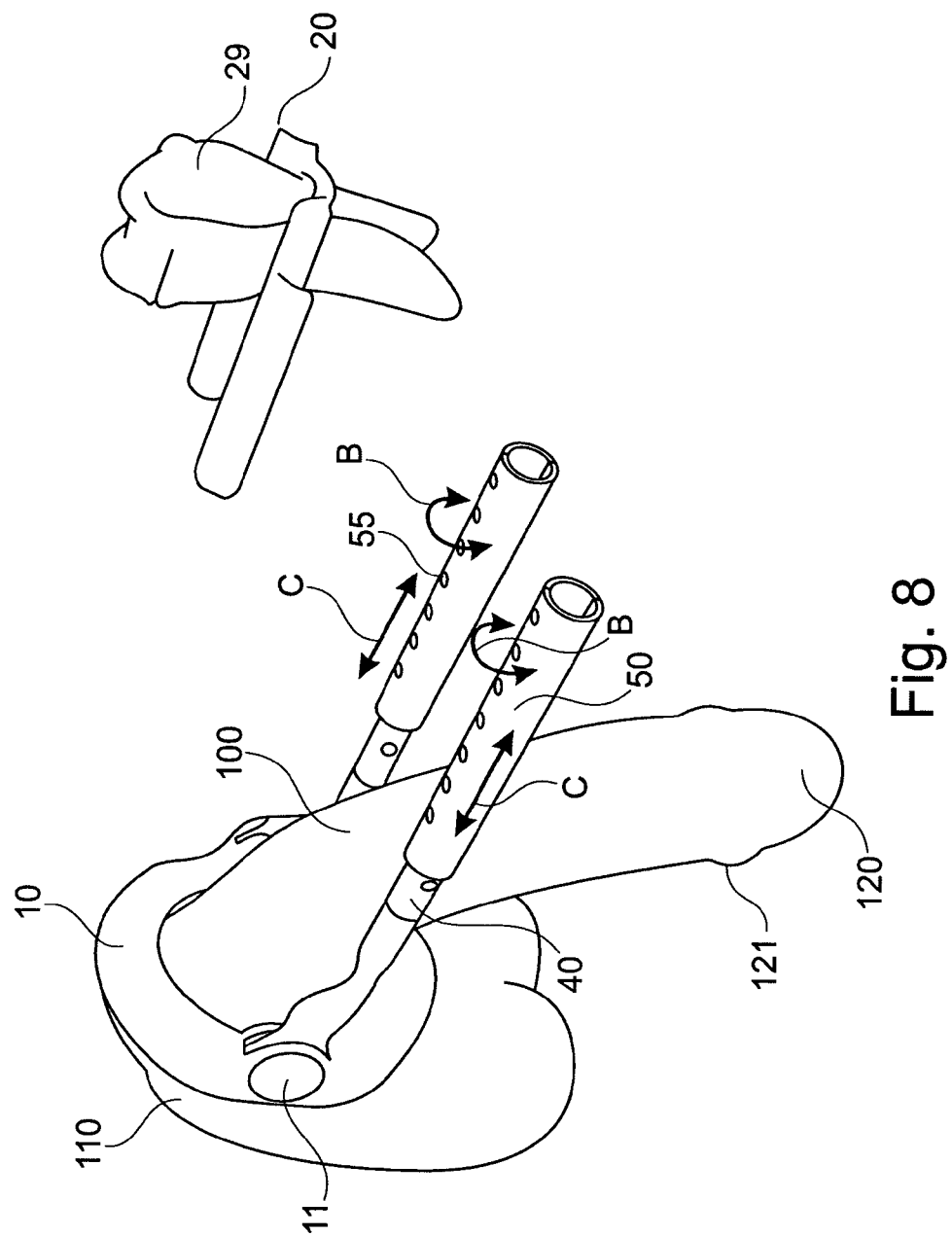
FIG. 8 shows a step of mounting an apparatus as shown in FIGS. 1-7 on a user.
Figure 9:
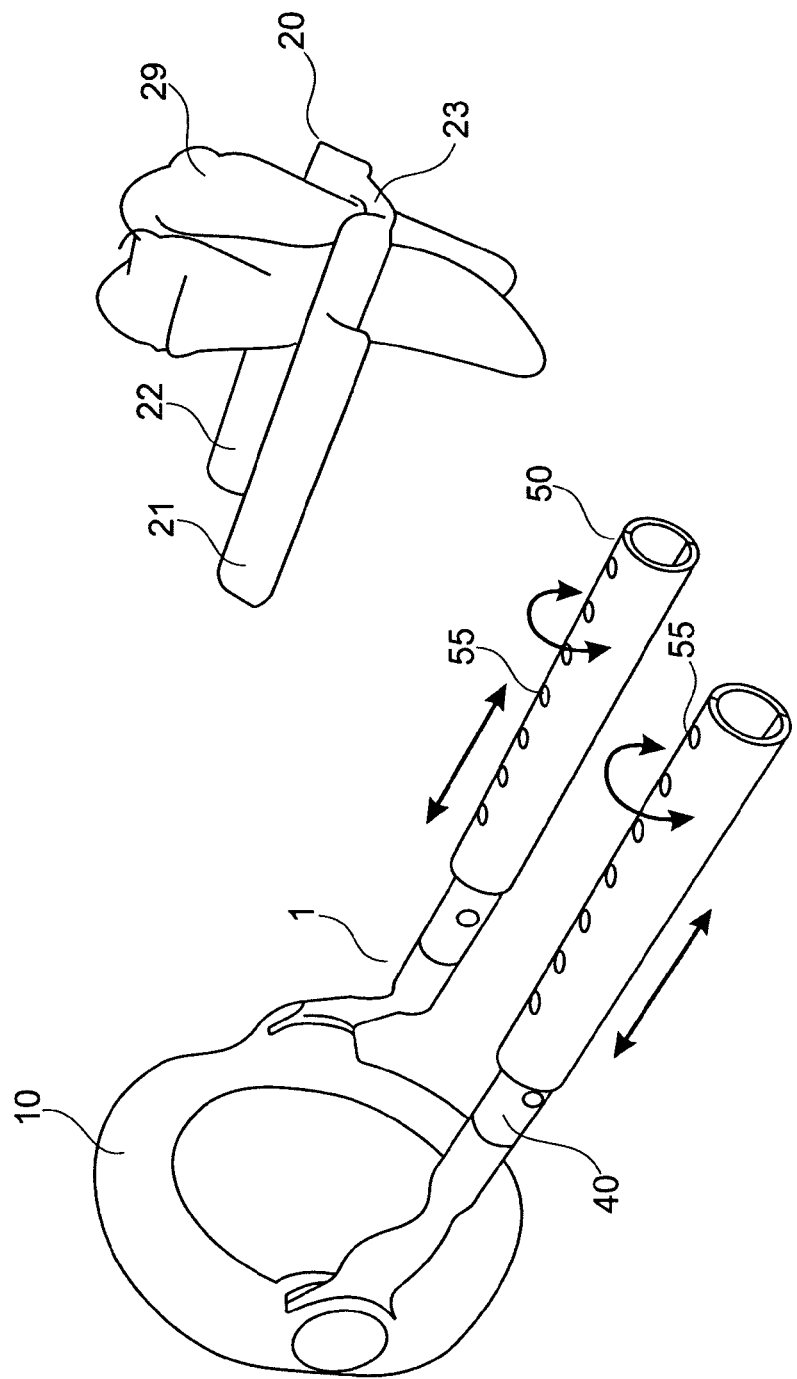
FIG. 9, is another view of the apparatus in FIG. 8.

The mounting of the apparatus 1, according to the embodiment, shown in FIGS. 1-10 may now be explained with reference especially to FIG. 8. In a first step the base 10 with the connection members 30 is fitted around the base 110 of the penis 100. Then the length of the penis 100 from the base 110 to the proximal side 121 of the glans 120 of the penis may be assessed by a user, and the length of the connection members 30 be adjusted accordingly, as also described above by releasing the locked position of the first to part 40 with respect to the second tube part 50 by turning the second tube 50 as indicated by arrows B in FIG. 8, and then sliding the second tube 50 to the desired lengthwise position in relation to first tube part 40, as indicated by arrows C. Then the fastening means 29 of the retaining member may be mounted around the penis 100 immediately behind the glans 120 and the retaining member may be secured to or mounted on the connection members 30, whereby the lengthwise position of the first tube part 40 with respect to the second tube part 50 is locked due to the engagement between the third engagement means 20 and the fourth (second) engagement means. As described above further adjustment of the length may be provided by choice of orientation of the retaining member 20. If the adjustment of the apparatus 1 is not correct, a proper adjustment may easily be provided by removing the retaining member 20 and repeating the above mentioned steps. This adjustment and readjustment may by the advantageous configuration according to the invention be provided easily by the user himself, without aid, and without use of tools. Further, the adjustment and readjustment may easily be obtained without loose extension parts.

In another embodiment (not shown) the third engagement means 25, e.g. in the form of a knob or protrusion on the retaining member 20 may cooperate with engagement means on both the first tube part 40 and the second tube part 50 to prevent rotation of the first tube part 40 with respect to the second tube part 50. If e.g. the length of the knob in the sliced tube was adapted to extend through one of a series of holes in the second tube 50 (to prevent longwise and/rotation of the second tube part 50 with respect to the retainer 20), and into an elongate slit or groove (parallel to elongate axis A) or a set of apertures in the inner, first tube part 40 (to prevent rotation of the first tube part), a releasable locking of the first and second tube parts relative to each other may be obtained in an apparatus having only a single connection member 30. This principle may however also be applied with two or more connection members 30.

With reference to FIGS. 11-19 an advantageous biasing mechanism for the apparatus 1 for applying traction to a penis 1 is described in the following.

The biasing mechanism comprises a second spring 70, preferably a helical spring, having a proximal end 71 and a distal end, the second spring 70 being arranged to between the first tube part 40 and the second tube part 50, to provide a biasing of the connection member 30 in a proximal direction, i.e. to provide a biasing of the retaining member 20 away from the base part 10.

The second spring 70 is located inside first tube part 40 surrounding a rod 69 extending proximally from the first spring 60. The distal end 72 of the second spring preferably engages a proximally facing surface 66 of a body part 67 of the first spring 60. Preferably, the main body part 67, the resilient arms 63, 64, the first engagement means 65 and the rod 69 are formed in one piece, e.g. in a plastic material.

The proximal end 71 of the second spring 70 engages a stop 43 on an inner surface of the first tube part 40. The stop 43 may be an annular protrusion on the inner surface of the first tube part or it may comprise a set of 1-6 discrete protrusions or knobs around said inner surface of the first tube part 40.

Since the first spring 60 can be locked with respect to sliding against the second tube part 50 (via first engagement means 65) as describe above, a biasing may thus be provided between the first tube part 40 and the second tube part 50.

Figure 12:
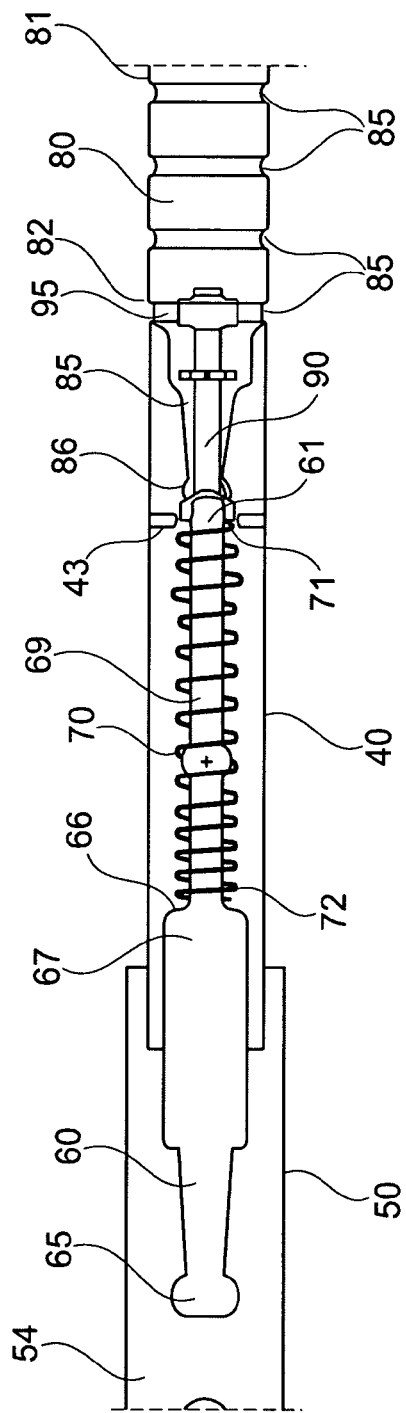
FIG. 12, shows a detailed, close up view of the biasing mechanism of the apparatus shown in FIG. 11.
Figure 13:
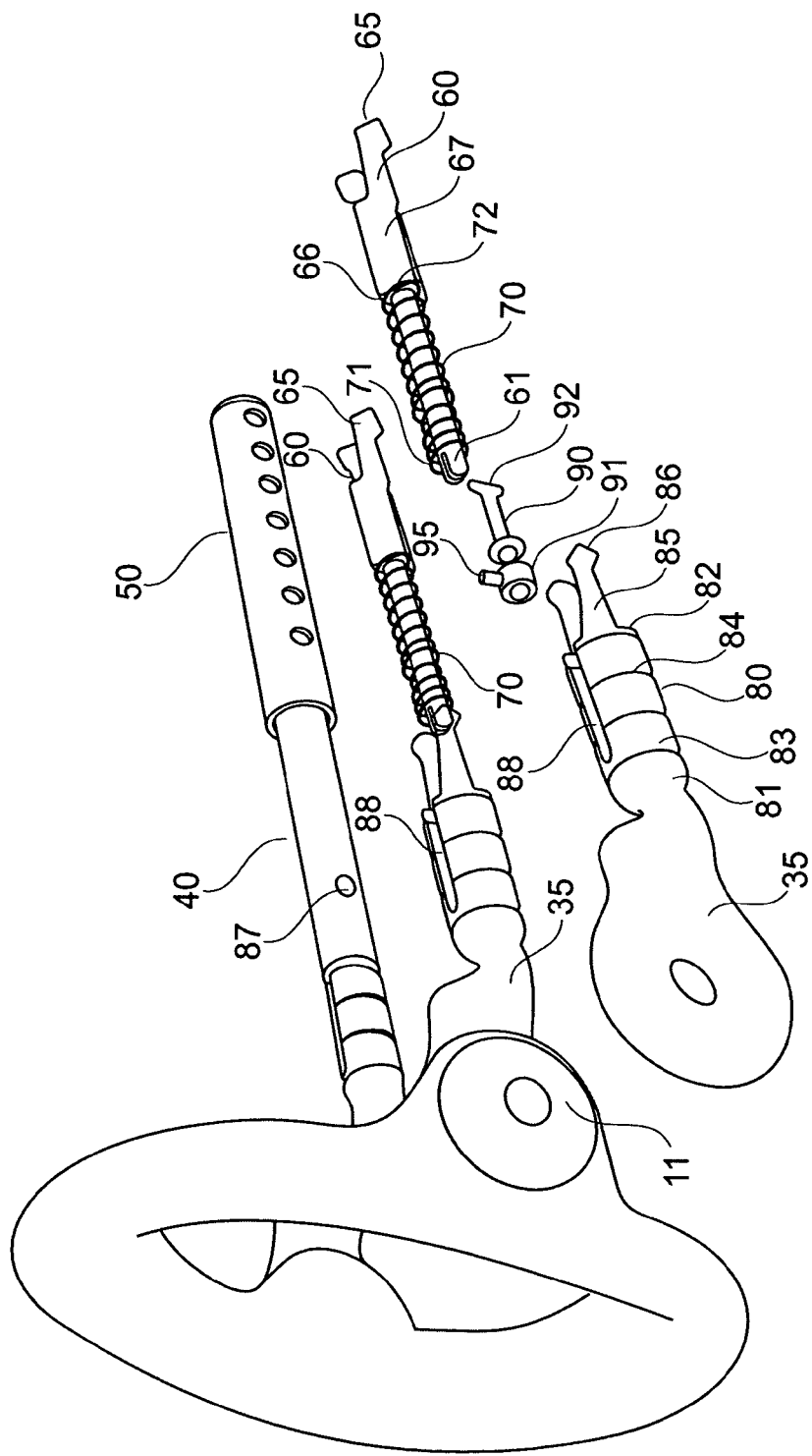
FIG. 13, in a perspective view, shows the apparatus of FIGS. 11 and 12, wherein a first and a second tube part are removed for viewing internal parts of one of two connection members. The figure further shows the same parts in a disassembled state.
Figure 14:
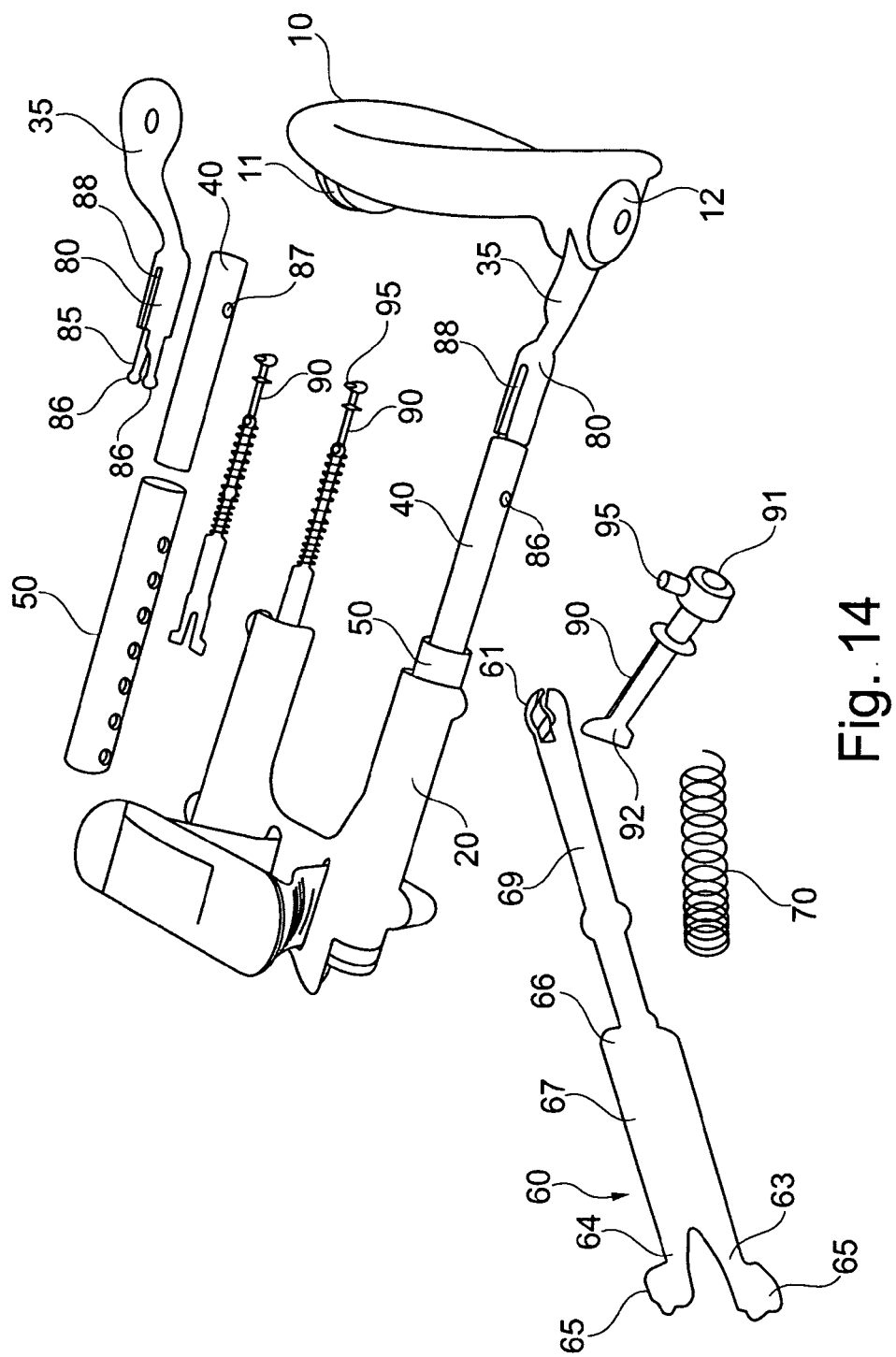
FIG. 14, in a perspective view, shows the apparatus of FIG. 13 from a different angle, and with a retaining member mounted on one connection arm, another connection member being shown in a partly disassembled state, the disassembled parts being shown newt to the apparatus.
Figure 15:
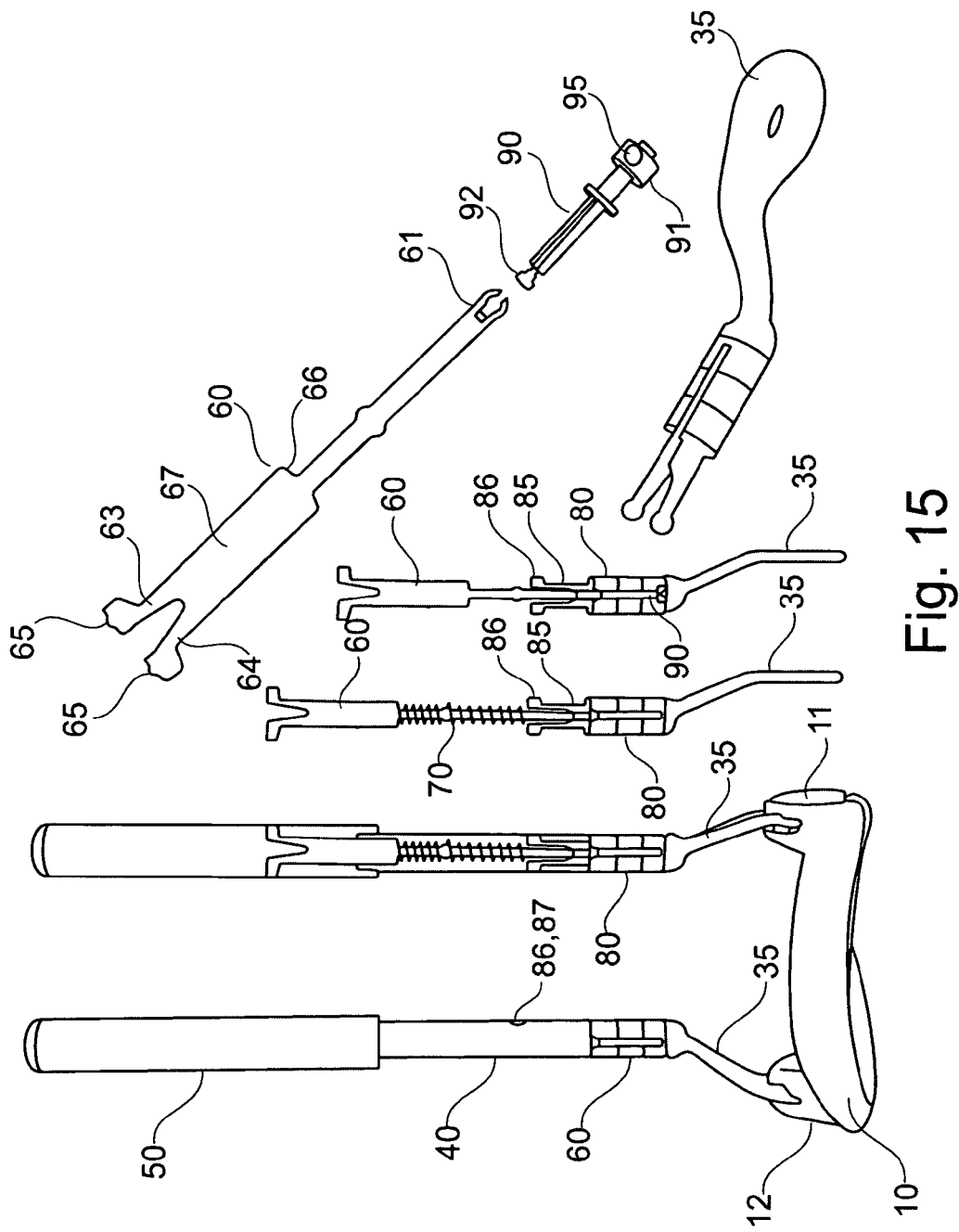
FIGS. 15-19, shows the apparatus and biasing mechanism of FIGS. 11-14 seen from different angles, and with different of the part in sections.
Figure 16:
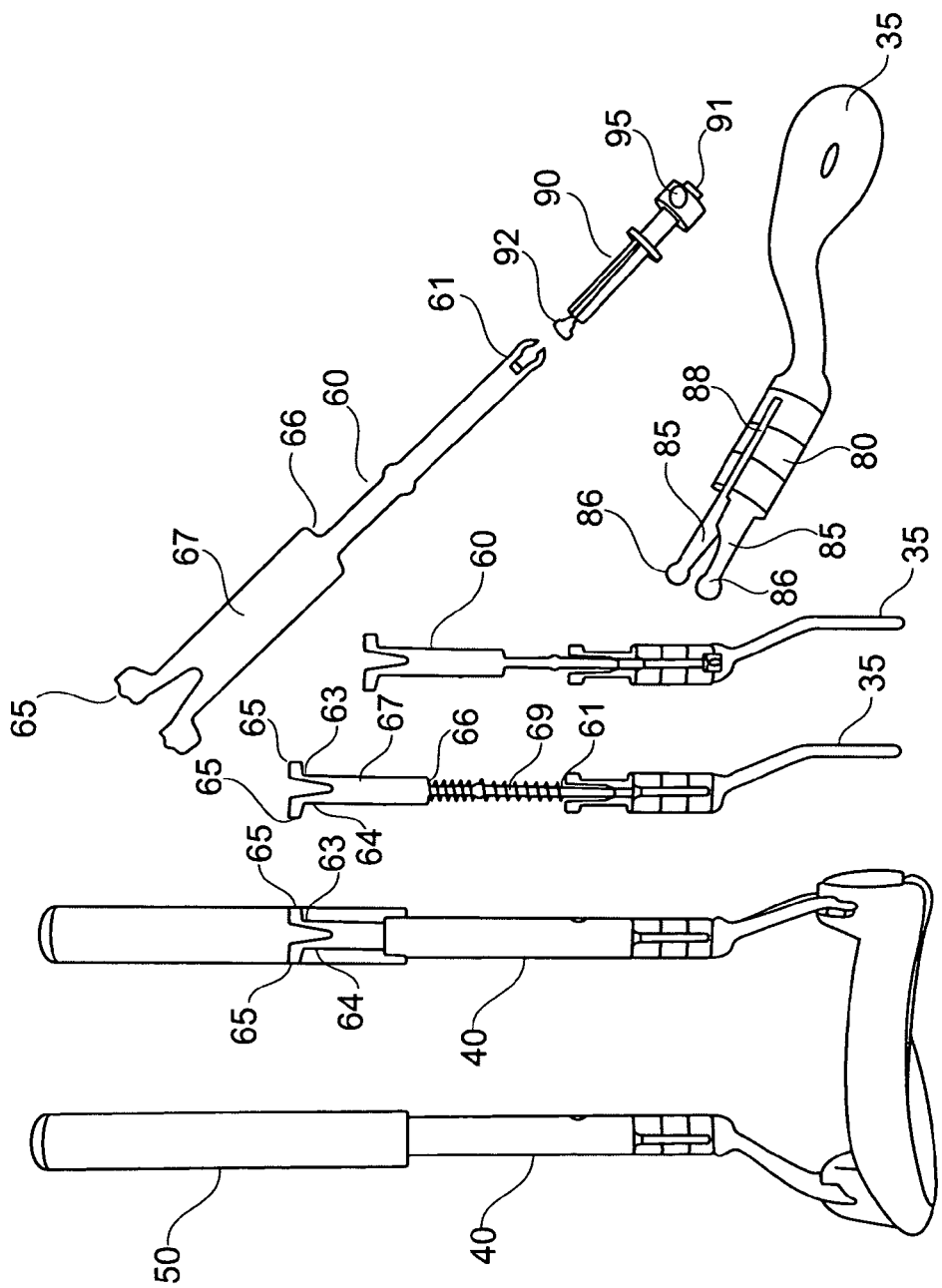
Figure 17:
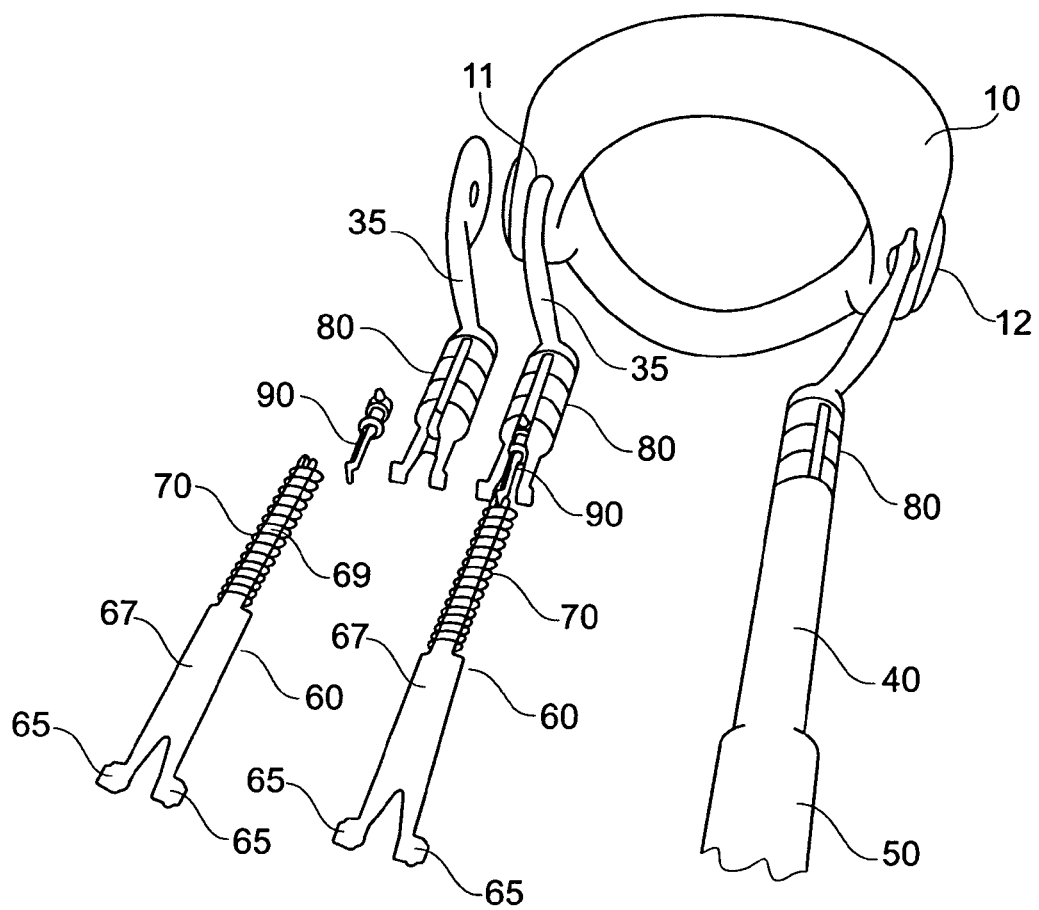
Figure 18:
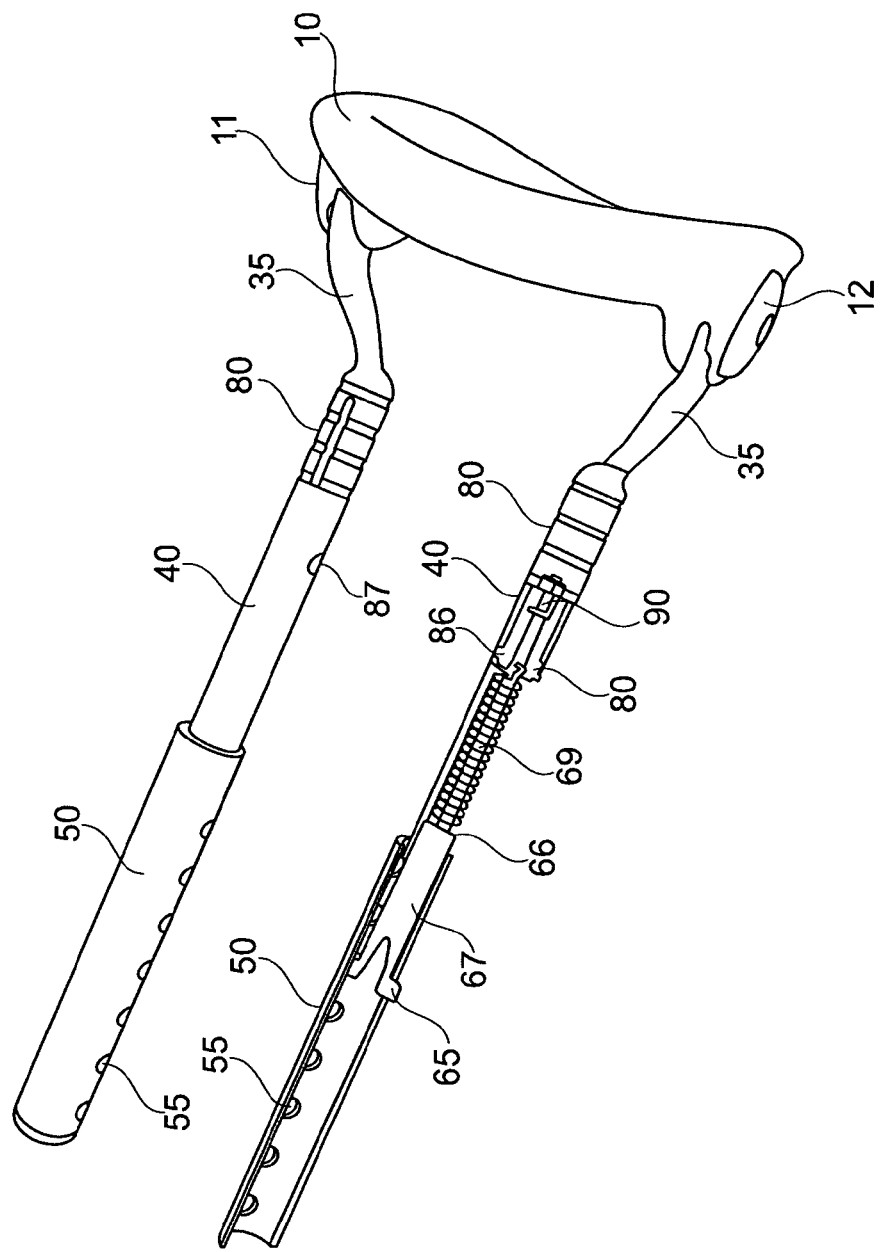
Figure 19:
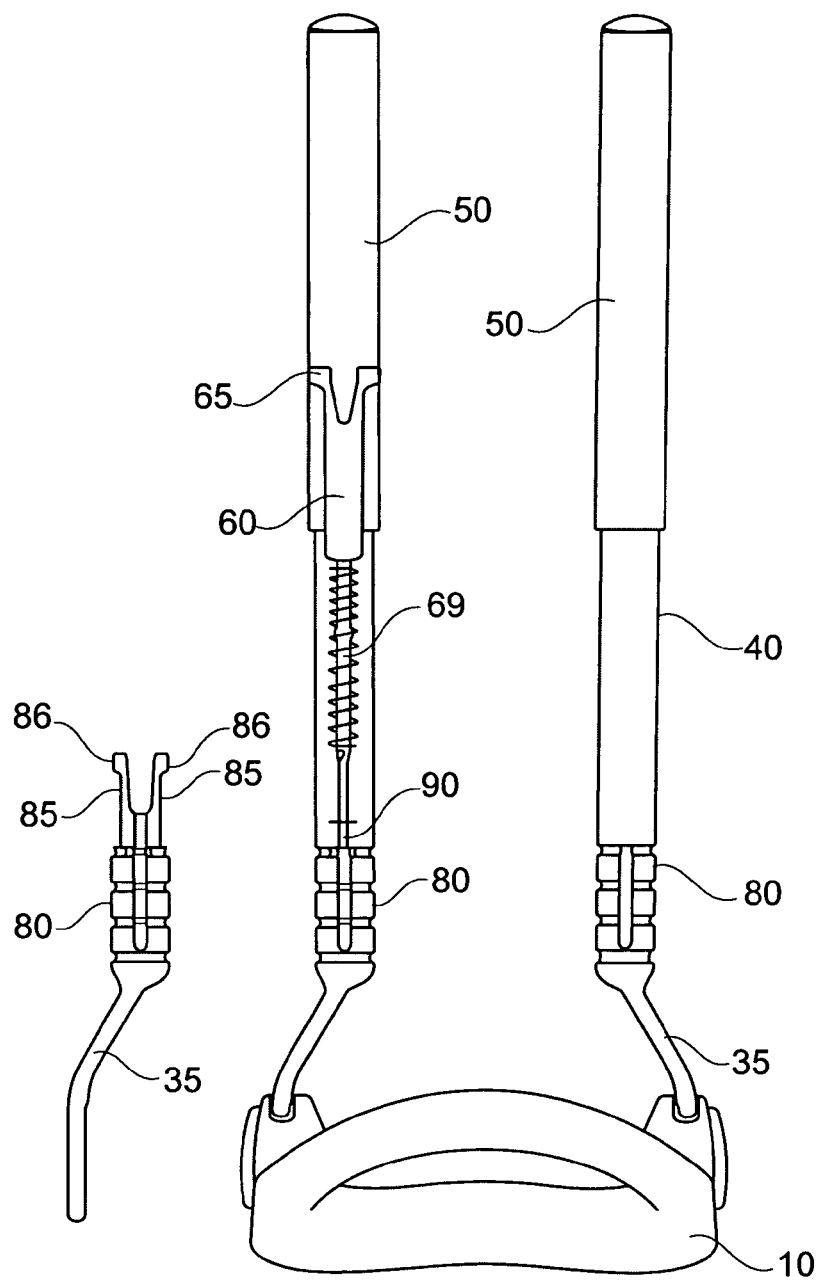

A proximal end 61 of the rod 69 may be adapted with a snap lock connection to lock to a first indicator piece 90. First indicator piece 90 constitutes a proximal extension of the rod 69 towards base member 10, and has a proximal end 91 and a distal end 92. Distal end 92 of the indicator piece is adapted to engage with the snap lock connection on the proximal end 61 of the rod 69, e.g. by a knob as shown in FIGS. 12 and 14. In other embodiments the split and knob locking connection between the distal end of the first indicator piece 90 and the proximal end 61 of the rod 69 may be on the opposite parts. Other, locking mechanisms may further be utilized.

An indicator tap 95 may further be provided on the indicator piece 90.

Since the first indicator piece 90 is locked to the rod 69 and thereby to the second tube part 50, the first indicator piece 90 is slidable with the second tube part 50 in relation to the first tube part 40, and may serve to provide the user with information of the load or biasing force provided by the second spring 70 as will be further explained below.

The first tube part 40 is preferably connected to the base part 10 via arm 35 and a second indicator piece 80. The second indicator piece has a proximal end 81 connected to the arm 35, and a distal end 82 connectable to the first tube part 40. The second indicator piece 80 is preferably connected to the first tube part 40 via resilient U shaped spring having knobs 86 formed at the distalmost end of each of a set of spring arm forming the U-shaped spring. The U-shaped spring provides a biasing of the knobs outward in a direction transversal to the elongate axis A of the connection members 30. The knobs 86 on the resilient arms of the U-shaped spring are adapted to cooperate with apertures 87 formed in the first tube part 40.

The second indicator piece 80, when mounted on the first tube part thus forms a proximal extension of the first tube part and provides a connection to the arm 35 and to the base member 10.

The second indicator piece 80 is hollow and adapted to slideably receive the first indicator piece 90 fully or partly.

The second indicator piece 80 may be formed in transparent material, e.g. a polymer material, such that at least parts of the first indicator piece 90, e.g. the indicator tap 95 or at least the proximal end 91 may be visible through the surface 83 the second indicator part. The surface 83 of the second indicator part may be formed with one or more indicators, e.g. in the form of stripes or annular protrusions or indentations 84 as shown in FIGS. 11-19. Alternatively or additionally a slit 88 may be formed through the second indicator part 80, in a direction parallel to the longitudinal axis A of the connection members. The slit 88 may be adapted to cooperate with the indicator tap 95 of the first indicator piece 90. In an alternative embodiment (not shown) the slit 88 may be provided with a transparent cover, so that the at least parts of the first indicator piece 90, e.g. the indicator tap 95 or at least the proximal end 91 of the piece 90 may be visible through the transparent cover.

In an embodiment (not shown) the first indicator piece 90 may be formed integrally with the rod 69 rather than being connected via the snap lock mechanism described above.

The above mentioned biasing mechanism in combination with the above mentioned adjustment facilities allow the user to adjust the pull or traction in the penis 100 from 0-3 kg.

Although the present invention has been described in connection with the specified embodiments, it should not be construed as being in any way limited to the presented examples. The scope of the present invention is set out by the accompanying claim set.

The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

LIST OF REFERENCES

A. Longitudinal axis of connection member
1. Apparatus for applying traction to a penis
10. Base member
11. Joint
12. Joint
20. (Glans) Retaining member
21. Sliced tube part
22. Sliced tube part
23. Body part of retaining member
25. Third engagement means
26. Openings in body part
27. Protrusions on glans fastening means 29
28. Handle on glans fastening means 29

29. Glans fastening means
30. (Telescoping) Connection member
31. Proximal (first) end of connection member
32. Distal (second) end of connection member
35. Arm
40. First tube part
41. Proximal end of first tube part
42. Distal end of first tube part
43. Stop
50. A second tube part
51. Proximal end of second tube part
52. Distal end end of second tube part
53. Plug
54. Inner wall of a the second tube part
55. Second engagement means (first plurality)
55'. Second engagement means (second plurality)
56. Outer wall of second tube part
60. A first spring assembly
61. Proximal end
63. Resilient arm (of first spring)
64. Resilient arm (of first spring)
65. First engagement means
66. Proximally facing surface
67. Body part
68. Rounded or inclined surface (on knob)
69. Rod
70. Second spring
71. Proximal end of spring
72. Distal end of spring
80. Second indicator piece
81. Proximal end of indicator piece
82. Distal end of indicator piece
83. Surface of indicator piece
84. Markings/indicator marks
85. Resilient arm
86. Knob on resilient arm
87. Aperture in first tube part 40
88. Slit
90. First indicator piece
91. Proximal end of indicator piece
92 Distal end of indicator piece
95. Indicator tap
100. Penis
110. Base of penis
120. Glans

The invention claimed is:

1. An apparatus (1) for applying traction to a penis (100) with, a base (110) and a glans (120), the apparatus comprising:
   a base member (10) adapted to be arranged around the base (110) of the penis (100);
   a retaining member (20) for fixation and support of the glans (120) of the penis (100); and
   at least one telescoping connection member (30) arranged between the base member (10) and the retaining member (20), the telescoping connection member (30) having a longitudinal axis (A);
   wherein the telescoping connection member (30) comprises:
   a first tube part (40) and a second tube part (50), the first tube part (40) being slidably arranged in the second tube part (50);
   a first spring (60) connected to the first tube part (40), the first spring (60) being compressible in a direction transverse to the longitudinal axis (A) of the telescoping connection member (30); and
   at least one first engagement means (65, 65') arranged on the spring (60), and a plurality of second engagement means (55, 55') arranged in the second tube part (50),
   wherein each first engagement means (65, 65') is adapted to engage any of the second engagement members (55, 55') so as to releasably lock the first tube part (40) against longitudinal movement relative to the second tube part (50),
   wherein each of the first engagement means (65) defines a knob, and each of the second engagement means (55) defines an aperture formed in an inner wall of the second tube part (50),
   wherein the knob (65) has a rounded and/or inclined surface (68), which facilitates travel of the knob (65) in a direction transverse to the longitudinal axis (A) of the telescoping connection member (30) against compression of the spring (60) when moving the first tube part (40) in relation to the second tube part (50),
   wherein the first tube part (40) is rotatable in relation to the second tube part (50), and wherein the inclined surface (68) extends in a direction parallel to the longitudinal axis (A) of the telescoping connection member (30), whereby relative rotation of the first and second tube parts (40,50) causes the knob (65) to move in a direction transverse to the longitudinal axis (A) of the telescoping connection member (30).

2. The apparatus (1) for applying traction to a penis (100) according to claim 1, wherein the spring (60) is U-shaped, having a set of resilient arms (63, 64) with first engagement means (65) arranged on each arm (63, 64), and where a first and second plurality of second engagement means (55, 55') are arranged oppositely in the second tube part (50).

3. An apparatus (1) for applying traction to a penis (100) with a base (110) and a glans (120), the apparatus comprising:
   a base member (10) adapted to be arranged around the based (110) of the penis (100);
   a retaining member (20) for fixation and support of the glans (120) of the penis (100); and
   at least one telescoping connection member (30) arranged between the base member (10) and the retaining member (20), the telescoping connection member (30) having a longitudinal axis (A);
   wherein the telescoping connection member (30) comprises:
   a first tube part (40) and a second tube part (50), the first tube part (40) being slidably arranged in the second tube part (50);
   a first spring (60) connected to the first tube part (40), the first spring (60) being compressible in a direction transverse to the longitudinal axis (A) of the telescoping connection member (30); and
   at least one first engagement means (65, 655 arranged on the spring (60), and a plurality of second engagement means (55, 55') arranged in the second tube part (50),
   wherein each first engagement means (65, 65') is adapted to engage any of the second engagement members (55, 55) so as to releasably lock the first tube part (40) against longitudinal movement relative to the second tube part (50),
   wherein the spring (60) is U-shaped, having a set of resilient arms (63, 64) with first engagement means (65) arranged on each arm (63, 64), and where a first and second plurality of second engagement means (55, 55') are arranged oppositely in the second tube part (50),
   wherein the retaining member (20) comprises third engagement means (25) adapted to cooperate with either of a plurality of fourth engagement means on the second tube part (50) and/or on the first tube part (40) to prevent rotation of the first tube part (40) with respect to the second tube part (50).

4. The apparatus (1) for applying traction to a penis (100) according to claim 3, having two telescoping connecting members (30) connectable to said retaining member (20), wherein a plurality of fourth engagement means are formed on each of the second tube parts (50), and where each of the retaining members (20) comprises third engagement means (25) each adapted to cooperate with either of the plurality of fourth engagement means on the second tube parts (50), such that the second tube parts (50) are prevented from rotation with respect to the first tube parts (40).

5. The apparatus (1) for applying traction to a penis (100) according to claim 4, wherein the third engagement means (25) are knobs, and the fourth third engagement means are apertures formed in the outer surface of the second tube part (50).

6. The apparatus (1) for applying traction to a penis (100) according to claim 5 wherein the fourth engagement means are apertures formed through the second tube part (50).

7. The apparatus (1) for applying traction to a penis (100) according to claim 6 wherein the fourth engagement means also serve as the second engagement means (55).

8. The apparatus (1) for applying traction to a penis (100) according to claim 3, wherein the retaining member (20) comprises at least one sliced tube part (21, 22) adapted to click-on at a second tube part (50) of a telescoping connecter member (30) to prevent rotation of the first tube part (40) with respect to the second tube part (50).

9. The apparatus (1) for applying traction to a penis (100) according to claim 8, wherein the third engagement means (25) is a knob formed on the inside of the sliced tube part (21, 22), adapted for engaging at least either of a plurality of fourth engagement members in the form of apertures on the second tube part (55) in order to prevent rotation of the second tube part 50 with respect to the first tube part (40), and wherein the sliced tube part (21, 22) has a first and a second end, and where the third engagement means (25) is formed in the proximity of either the first or the second end.

10. The apparatus (1) for applying traction to a penis (100) according to claim 3, having one telescoping connecting member (30), with a first and second tube (40, 50) connected rotatably with respect to each other, wherein the fourth engagement means comprises a plurality of apertures formed through the second tube part, and a plurality of apertures or an elongate groove formed in the outer surface of the first tube part (40), and where the third engaging means (25) is a knob adapted to extend though either of the apertures in the second tube part (50) and engage with the groove or either of the plurality of apertures formed in the outer surface of the first tube part (40).

11. The apparatus (1) for applying traction to a penis (100) according to claim 3, wherein said retaining member (20) comprises:

a first end (131) and a second end (132) opposite said fist end;

connecting means (21, 22) for releasably connecting said retaining member to the distal end of said connection member (30), the connecting means (21, 22) being arranged at the first, end (131) of said retaining member, and comprising locking means (25) for locking the retaining member (20) against movement relative to the connecting member along the longitudinal axis in at least one direction; and glans fastening means (26, 29) which is arranged at the second end (132) of said retaining member (20).

12. The apparatus (1) for applying traction to a penis (100) according to claim 11, wherein the locking means (25) defines a knob or an aperture cooperating with a corresponding aperture or knob, respectively, on the connection member (30) so as to lock the retaining member (20) relative to the connecting member (30).

13. The apparatus (1) for applying traction to a penis (100) according to claim 12, the retaining member (20) is adapted to allow a user to fasten the connection member (30) in either of:

a first position in which the first end (131) is positioned closer to the base member (20) than the second end (132), or a second position in which the second end (132) is positioned closer to the base member (20) than the first end (131).

* * * * *